US011103605B2

(12) United States Patent
Donnelly et al.

(10) Patent No.: US 11,103,605 B2
(45) Date of Patent: *Aug. 31, 2021

(54) PET-IMAGING IMMUNOMODULATORS

(71) Applicant: BRISTOL-MYERS SQUIBB COMPANY, Princeton, NJ (US)

(72) Inventors: David J. Donnelly, Doylestown, PA (US); Kenneth M. Boy, Durham, CT (US); Yunhui Zhang, Princeton, NJ (US); Joonyoung Kim, Princeton, NJ (US); Adrienne Pena, South Plainfield, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/098,765

(22) PCT Filed: May 17, 2017

(86) PCT No.: PCT/US2017/033004
§ 371 (c)(1),
(2) Date: Nov. 2, 2018

(87) PCT Pub. No.: WO2017/201111
PCT Pub. Date: Nov. 23, 2017

(65) Prior Publication Data
US 2019/0117801 A1    Apr. 25, 2019

Related U.S. Application Data

(60) Provisional application No. 62/338,872, filed on May 19, 2016.

(51) Int. Cl.
*A61K 51/08* (2006.01)
*A61B 6/03* (2006.01)
*A61B 6/12* (2006.01)
*C07K 7/08* (2006.01)

(52) U.S. Cl.
CPC ............ *A61K 51/088* (2013.01); *A61B 6/037* (2013.01); *A61B 6/12* (2013.01); *C07K 7/08* (2013.01); *C07B 2200/05* (2013.01)

(58) Field of Classification Search
None
See application file for complete search history.

(56) References Cited

U.S. PATENT DOCUMENTS

| | | | |
|---|---|---|---|
| 5,869,451 A | 2/1999 | Dower et al. | |
| 9,090,668 B2 | 7/2015 | Suga et al. | |
| 9,308,236 B2 | 4/2016 | Miller et al. | |
| 9,410,148 B2 | 8/2016 | Suga et al. | |
| 9,732,119 B2 | 8/2017 | Sun et al. | |
| 9,809,625 B2 | 11/2017 | Boy et al. | |
| 9,850,283 B2 | 12/2017 | Miller et al. | |
| 9,856,292 B2 | 1/2018 | Gillman et al. | |
| 9,861,680 B2 | 1/2018 | Mapelli et al. | |
| 9,879,046 B2 | 1/2018 | Miller et al. | |
| 9,944,678 B2 | 4/2018 | Sun et al. | |
| 10,143,746 B2 | 12/2018 | Allen et al. | |
| 2010/0168380 A1 | 7/2010 | Suga et al. | |
| 2013/0178394 A1 | 7/2013 | Suga et al. | |
| 2014/0018257 A1 | 1/2014 | Suga et al. | |
| 2016/0137696 A1* | 5/2016 | Gillman ............... | A61K 51/088 424/278.1 |
| 2016/0222060 A1 | 8/2016 | Miller et al. | |
| 2017/0260237 A1 | 9/2017 | Miller et al. | |
| 2017/0283462 A1 | 10/2017 | Miller et al. | |
| 2017/0283463 A1 | 10/2017 | Miller et al. | |
| 2017/0369530 A1 | 12/2017 | Miller et al. | |
| 2018/0086793 A1 | 3/2018 | Gillman et al. | |

FOREIGN PATENT DOCUMENTS

| | | |
|---|---|---|
| WO | WO-200026353 A1 | 5/2000 |
| WO | WO-2010027828 A2 | 3/2010 |
| WO | WO-2011161699 A2 | 12/2011 |
| WO | WO-2012168944 A1 | 12/2012 |
| WO | WO-2013010573 A1 | 1/2013 |
| WO | WO-2013144704 A1 | 10/2013 |
| WO | WO-2013182240 A1 | 12/2013 |
| WO | WO-2013183707 A1 | 12/2013 |
| WO | WO-2014151006 A2 | 9/2014 |
| WO | WO-2015033303 A1 | 3/2015 |
| WO | WO-2015044900 A1 | 4/2015 |
| WO | WO-2016-086021 A1 | 6/2016 |
| WO | WO-2016-086036 A1 | 6/2016 |
| WO | WO-2017-210335 A1 | 12/2017 |

(Continued)

OTHER PUBLICATIONS

Hayashi, Y., et al., "In Vitro Selection of Anti-Akt2 Thioether-Macrocyclic Peptides Leading to Isoform-Selective Inhibitors," ACS Chemical Biology 7(3):607-613, American Chemical Society, United States (Mar. 2012).

Hoyer, K.M., et al., "The Iterative Gramicidin S Thioesterase Catalyzes Peptide Ligation and Cyclization," Chemistry & Biology 14(1):13-22, Elsevier, United States (Jan. 2007).

Karle, I. L., "Conformation of Cyclic Pentapeptides in the Crystalline State. Cyclic (D-Phe-L-Pro-Giy-D-Aia-L-Pro) with 3.fwdarw. 1 and 4.fwdarw. 1 Intramolecular Hydrogen Bonds", Database Accession No. 1981: 498291; Compound 78221-87-1.

(Continued)

*Primary Examiner* — Jennifer Lamberski
(74) *Attorney, Agent, or Firm* — Sterne, Kessler, Goldstein & Fox P.L.L.C.

(57) ABSTRACT

The invention relates to the synthesis and use of $^{18}$F-labeled millamolecules for imaging various processes within the body, for detecting the location of molecules associated with disease pathology, and for monitoring disease progression are disclosed.

11 Claims, 4 Drawing Sheets

(56) References Cited

FOREIGN PATENT DOCUMENTS

| WO | WO-2018-085750 A2 | 5/2018 |
| WO | WO-2018-237153 A1 | 12/2018 |
| WO | WO2019-070643 A1 | 4/2019 |

OTHER PUBLICATIONS

Morimoto, J., et al., "Discovery of Macrocyclic Peptides Armed with a Mechanism-Based Warhead: Isoform-Selective Inhibition of Human Deacetylase SIRT2," Angewandte Chemie International Edition, 51(14):3423-3427, Wiley-VCH, Germany (Apr. 2012).

Rothe, M., et al., "Interchain Reactions (Cyclo-Oiigomerizations) During the Cyclization of Resin-Bound Peptides," Database Accession No. 1978: 424771; Compound RN: 66517-17-7.

Cook, J.W., et al., "Crystal Structure and Conformation of the Cyclic Trimer of a Repeat Pentapeptide of Elastin, cyclo-(L-valyl-L-prolylglycyl-L-valylglycyl)$_3$," Journal of the American Chemical Society 102(17): 5502-5505 (Aug. 1980).

Tamaki, M., et al., "Cyclization of Penta- and Hexapeptide Active Esters Related to Gramicidin S and Gratisin," Bulletin of the Chemical Society of Japan 62(2):594-596 (Feb. 1989).

Yamagishi, Y., et al., "Natural Product-Like Macrocyclic N-Methyl-Peptide Inhibitors against a Ubiquitin Ligase Uncovered from a Ribosome-Expressed De Novo Library," Chemistry & Biology 18(12):1562-1570, Elsevier, United States (Dec. 2011).

Maute, R., et al., "Engineering High-Affiinity PD-1 Variants for Optimized Immunotherapy and Immune-PET Imaging," Proceedings of the National Academy of Sciences of the United States of America, 112, E6506-E6514, (Nov. 2015).

Michel, K et al. "Development and Evaluation of Endothelin-A Receptor (Radio) Ligands for Positron Emission Tomography." J. Med. Chem., 54:939-948.(2011).

Schrigten, D et al. "A New Generation of Radiofluorinated Pyrimidine-2,4,6-triones as MMP-Targeted Radiotracers for Positron Emission Tomography." J. Med. Chem, 55:223-232. (2012).

Inkster, J et al. "2-Fluoropyridine prosthetic compounds for the 18F labeling of bombesin analogs." Bioorg. Med. Chem. Lett, 23:3920-3926. (2013).

\* cited by examiner

2A. Saline (0 mg/kg PD-L1 binding macrocyclic peptide)

2B. Pre-dose of 60 mg/kg of PD-L1 binding macrocyclic peptide

PET-IMAGING IMMUNOMODULATORS

CROSS REFERENCE TO RELATED APPLICATION

This application claims priority to U.S. Provisional Patent Application Ser. No. 62/338,872 filed May 19, 2016, which is incorporated by reference in its entirety.

The present disclosure generally relates to immunomodulators containing $^{18}$F-prosthetic groups and the synthesis and use of $^{18}$F-labeled immunomodulators for imaging various processes within the body, for detecting the location of molecules associated with disease pathology, and for monitoring disease progression.

Positron emission tomography (PET) is a non-invasive imaging technique that has become one of the most widely used methods in diagnostic medicine and drug development, with high sensitivity (fmoles), high resolution (4-10 mm) and tissue accretion that can be quantitated. The valuable in vivo functional information about biological processes in living subjects provided by PET imaging also provides a unique translational medical advantage in that the same tool can be used both preclinically and clinically.

PET relies on the design and synthesis of molecules labeled with a positron-emitting radioisotopes including $^{18}$F, $^{64}$Cu, $^{11}$C, $^{15}$O, $^{13}$N, $^{66}$Ga, $^{68}$Ga, $^{76}$Br, $^{89}$Zr, $^{94m}$Tc, $^{86}$Y and $^{124}$I. In vivo, these radiotracers or radioligands emit positrons from the nucleus of the isotope with different energies depending on the isotope used. The energy of the ejected positron controls the average distance that it travels before it collides with an electron resulting in the emission of two 511 keV gamma rays in opposite directions. The gamma rays produced by this positron annihilation event are detected by the PET imaging scanner to produce planar and tomographic images that reveal distribution of the radiotracer as a function of time. Accordingly, isotopes that are pure positron emitters with low ejection energy isotopes are preferred for PET imaging to minimize the distance traveled by the positron before annihilation and dosimetry problems caused by other emissions such as gamma rays, alpha particles or beta particles.

In addition, the half-life of the isotope used in PET imaging must be long enough to allow synthesis and analysis of the radiotracer molecule, injection into the patient, in vivo localization, clearance from non-target tissues, and the production of a clear image. $^{18}$F($\beta^+$635 keV 97%, $t_{1/2}$ 110 min) is one of the most widely used PET emitting isotopes because of its low positron emission energy, lack of side emissions and suitable half-life.

The present disclosure relates to a millamolecule substituted with an $^{18}$F-labeled prosthetic group that contains a nitro-pyridine linked to a polyethylene glycol (PEG) moiety and a terminal azide. In certain embodiments, millamolecules containing bifunctional conjugating moieties (e.g., with ring constrained alkyne groups) form covalent bonds with the terminal azide of the $^{18}$F-labeled prosthetic group via a "click" biorthogonal reaction to produce radiolabeled probes that are stable under physiological conditions. The UV absorbance of the resultant product further provides a practical, sensitive and rapid analytical method for determining the radiochemical purity of the product. These 18F labelled millamolecules are useful for detecting the presence of PD-L1 in cells and tissues such as tumors which can provide valuable treatment information.

Other features and advantages of the present disclosure will be apparent from the following detailed description and examples, which should not be construed as limiting.

Figure 1:
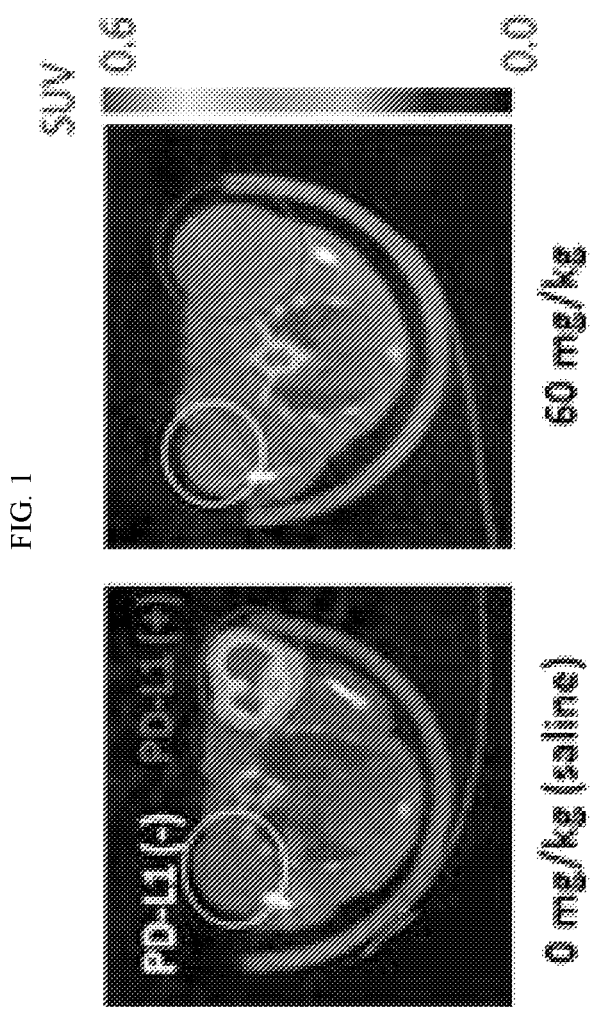
FIG. 1 is a representative PET/CT images of [$^{18}$F]labelled macrocyclic PD-L1 peptide in mice bearing bilateral PD-L1 (+) L2987 and PD-L1 (−) xenograft tumors.

In its first aspect the present disclosure provides a compound of formula (I)

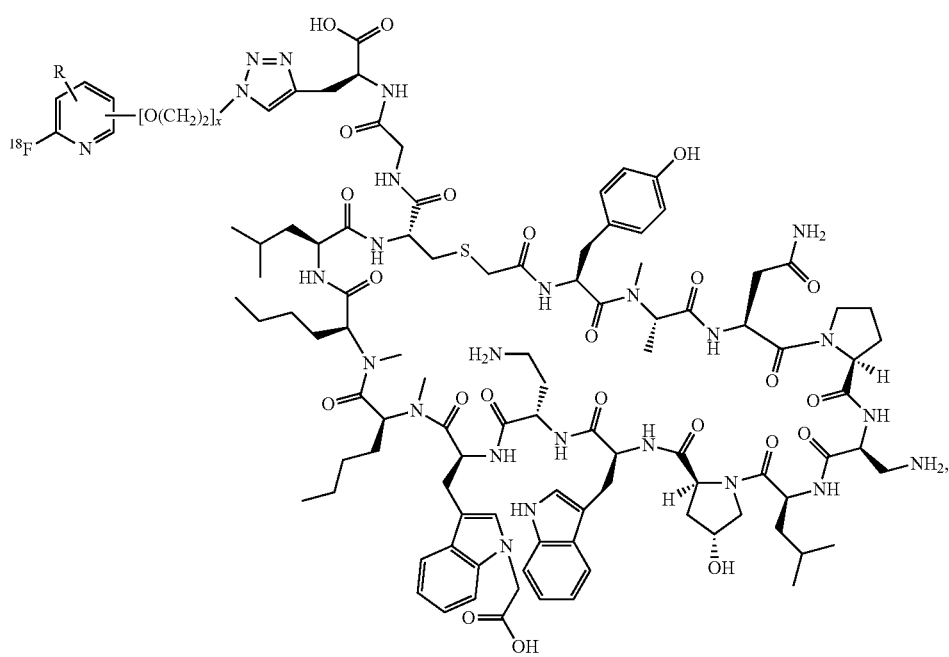

(I)

or a pharmaceutically acceptable salt thereof, wherein x is an integer from 1 to 8 and R is a $C_1$-$C_6$alkyl group.

In a second aspect the present disclosure provides a compound of formula (II)

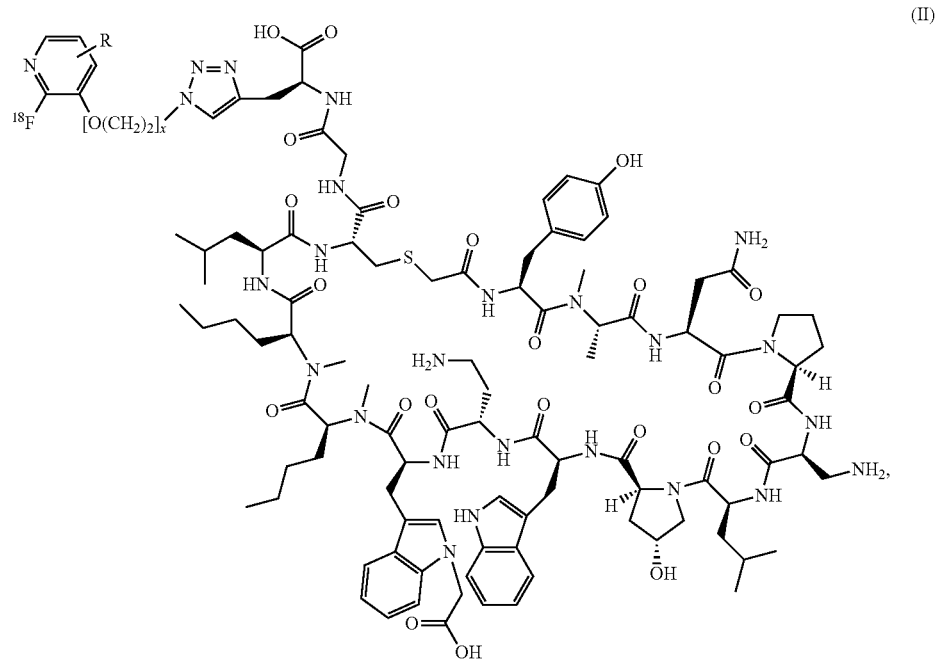

(II)

or a pharmaceutically acceptable salt thereof, wherein x is an integer from 1 to 8 and R is $C_1$-$C_6$alkyl group.

In a third aspect the present disclosure provides a compound of formula (III)

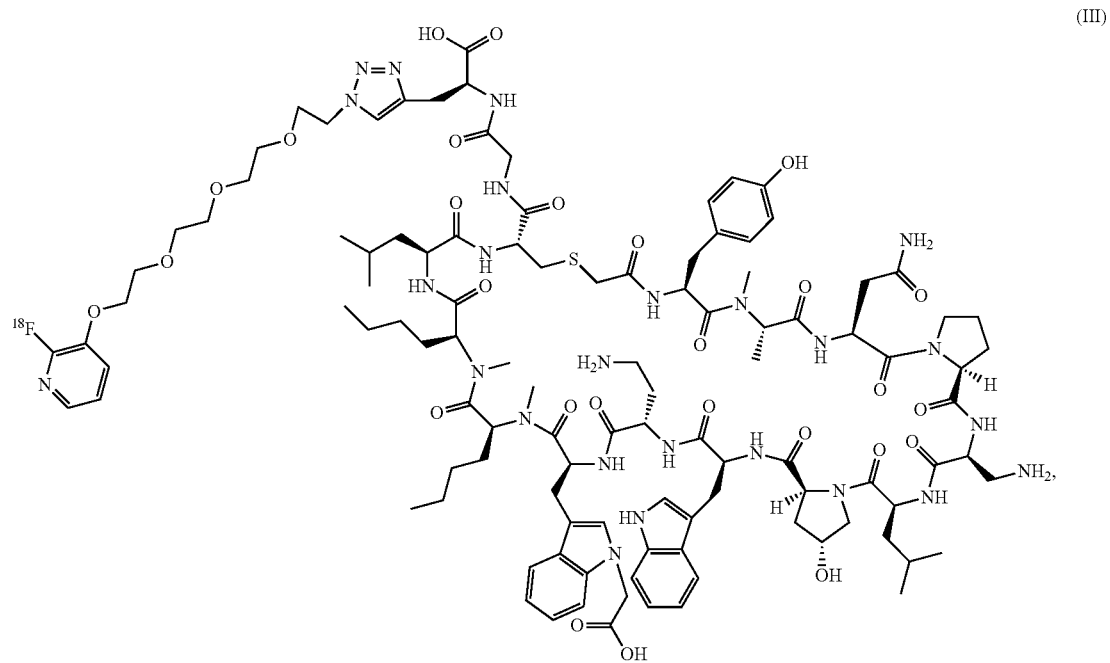 [SMILES: CCCC[C@H]1C(=O)N(C)[C@@H](CCCC)C(=O)N[C@@H](CC(C)C)C(=O)N[C@H](C(=O)NCC(=O)N[C@@H](Cc2cn(CCOCCOCCOCCOc3cccnc3[18F])nn2)C(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

(III)

or a pharmaceutically acceptable salt thereof.

In a fourth aspect the present disclosure provides a compound of formula (IV)
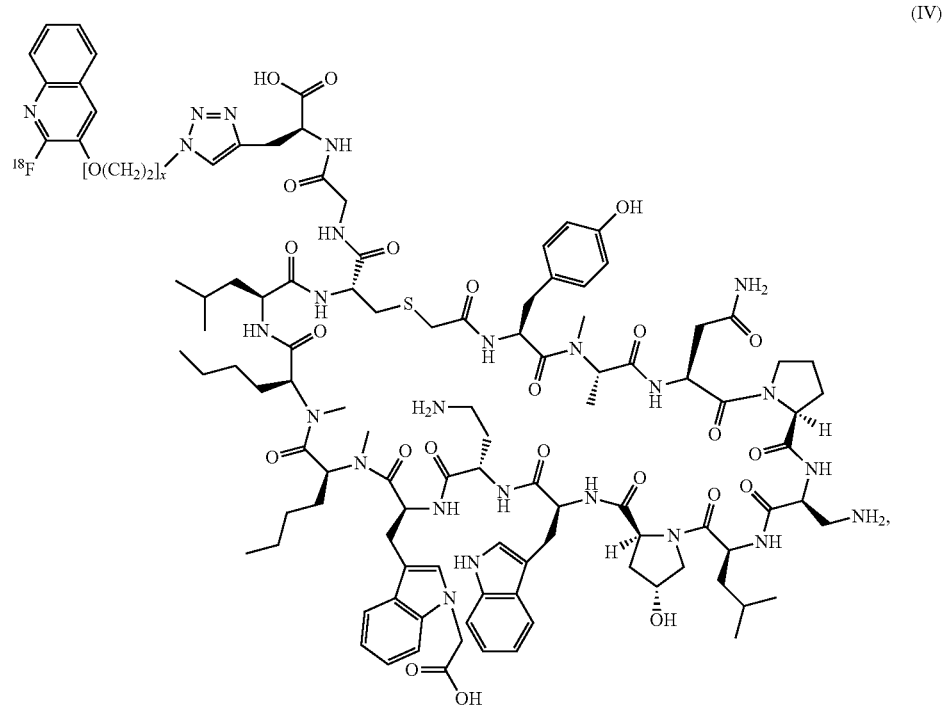
(IV)
or a pharmaceutically acceptable salt thereof, wherein x is an integer from 1 to 8 and R is $C_1$-$C_6$alkyl group.
In a fifth aspect the present disclosure provides a compound of formula (V)
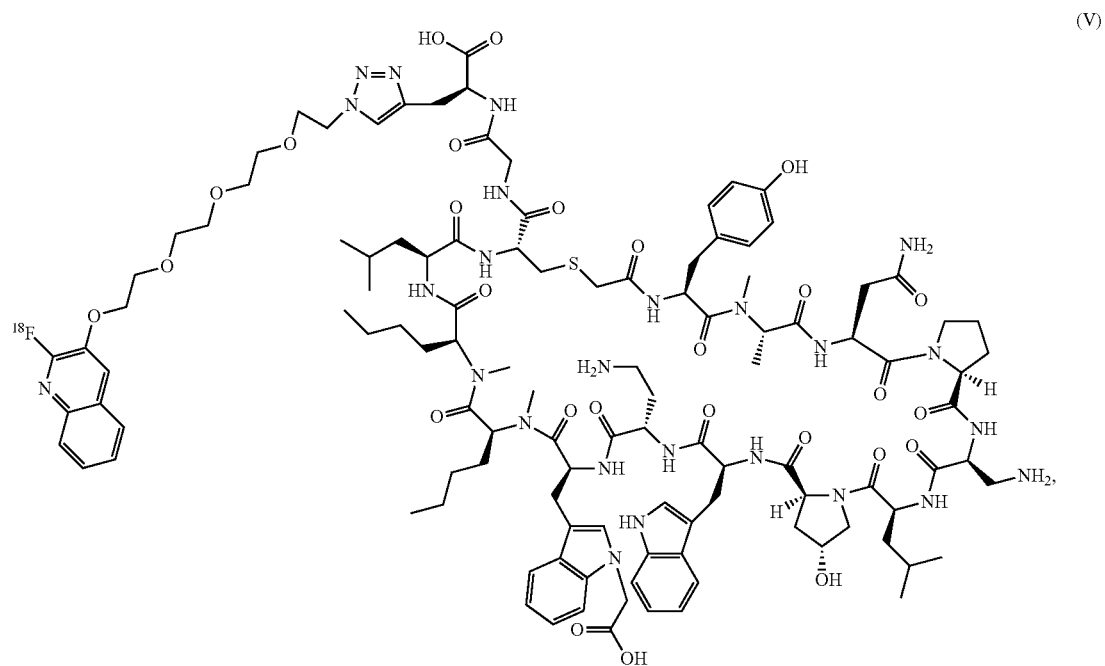 [SMILES: CCCC[C@H]1C(=O)N(C)[C@@H](CCCC)C(=O)N[C@@H](CC(C)C)C(=O)N[C@H](C(=O)NCC(=O)N[C@@H](Cc2cn(CCOCCOCCOCCOc3cc4ccccc4nc3[18F])nn2)C(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]
(V)
or a pharmaceutically acceptable salt thereof.

In a sixth aspect the present disclosure provides a method of obtaining an image of a compound of formula (I)-(V), or a pharmaceutically acceptable salt thereof, the method comprising, a) administering the compound to a subject; and
b) imaging in vivo the distribution of compound by positron emission tomography (PET) scanning.

In a first embodiment of the sixth aspect the imaged distribution of the compound of formula (I)-(V), or a pharmaceutically acceptable salt thereof, is indicative of the presence or absence of a disease.

In a seventh aspect the present disclosure provides a method of monitoring the progress of a disease in a subject, the method comprising (a) administering to a subject in need thereof a compound of formula (I)-(V), or a pharmaceutically acceptable salt thereof, which binds to a target molecule associated with the presence of the disease at a first time point and obtaining an image of at least a portion of the subject to determine the amount of the diseased cells or tissue; and (b) administering to the subject compound at one or more subsequent time points and obtaining an image of at least a portion of the subject at each time point; wherein the dimension and location of the diseased cells or tissue at each time point is indicative of the progress of the disease.

In an eighth aspect the present disclosure provides a method of quantifying diseased cells or tissues in a subject, the method comprising (a) administering to a subject having diseased cells or tissues a compound of formula (I)-(V) or a pharmaceutically acceptable salt thereof which binds to a target molecule located with the diseased cells or tissues; and (b) detecting radioactive emissions of the $^{18}$F in the diseased cells or tissue, wherein the level and distribution of the radioactive emissions in the diseased cells or tissues is a quantitative measure of the diseased cells or tissues.

In a first embodiment of the eighth aspect the disease is selected from the group consisting of solid cancers, hematopoietic cancers, hematological cancers, autoimmune disease, neurodegenerative disease cardiovascular disease, and pathogenic infection.

In a ninth aspect the present disclosure provides a method of obtaining a quantitative image of tissues or cells expressing PD-L1, the method comprising contacting the cells or tissue with a compound of formula (I)-(V) or a pharmaceutically acceptable salt thereof which binds to PD-L1, and detecting or quantifying the tissue expressing PD-L1 using positron emission tomography (PET).

In a tenth aspect the present disclosure provides a method of screening for an agent for treating a disease comprising the steps of (a) contacting cells expressing PD-L1 with a compound of formula (I)-(V) or a pharmaceutically acceptable salt thereof which binds to PD-L1 in the presence and absence of a candidate agent; and (b) imaging the cells in the presence and absence of the candidate agent using positron emission tomography (PET), wherein a decrease in the amount of radioactive emissions in the presence of the candidate agent is indicative of that the agent binds to PD-L1.

In an eleventh aspect the present disclosure provides a diagnostic agent or a pharmaceutical composition comprising a compound of formula (I) or a pharmaceutically acceptable salt thereof.

In a twelfth aspect the present disclosure provides a kit comprising the reaction precursors for use in producing the compound of formula (I), and instructions for producing the compound of formula (I) or a pharmaceutically acceptable salt thereof.

In another aspect, the present disclosure provides a compound according to formula (I)-(V) or a pharmaceutically acceptable salt thereof for use as an imaging agent.

In another aspect, the present disclosure provides a compound according to formula (I)-(V) or a pharmaceutically acceptable salt thereof for use in diagnosing a disease in a subject. Typically, the diagnosis includes the detection or monitoring of the progress of a disease in a subject. According to one embodiment, the compound according to formula (I)-(V) is administered to the subject requiring the diagnosis and direct visualization of the diseased cells and tissues is carried out using positron emission tomography.

In another aspect, the present disclosure provides a method of diagnosing ex-vivo a disease in a subject which is related to the level and distribution in tissues and cells of PD-L1 expression using a compound of formula (I)-(V) or a pharmaceutically acceptable salt thereof.

In another aspect, the present disclosure provides a method of monitoring in-vitro the progress of a disease in a subject, the method comprising:

(a) at a first time point; contacting a sample of cells or tissues of one subject with a compound of formula (I)-(V) wherein the compound binds to a target molecule associated with the presence of the disease and obtaining an image using positron emission tomography; and (b) at one or more subsequent time points, contacting another sample of cells or tissues with a compound of formula (I)-(V) and obtaining an image at each time point;

wherein the dimension and location of the diseased cells or tissue at each time point is indicative of the progress of the disease.

In another aspect, the present disclosure provides a method of quantifying in-vitro diseased cells or tissues in a subject, the methods comprising:

(a) contacting a sample of cells or tissues of one subject with a compound of formula (I)-(V) wherein the compound binds to a target molecule associated with the presence of the disease and obtaining an image using positron emission tomography; and (b) detecting radioactive emissions of the $^{18}$F in the diseased cells or tissue, wherein the level and distribution of the radioactive emissions in the diseased cells or tissues is a quantitative measure of the diseased cells or tissues.

According to one embodiment of any of the aspects of the present disclosure, the disease is related to the level and distribution in tissues and cells expressing PD-L1. Typically, the disease is selected from the group consisting of solid cancers, hematopoietic cancers, hematological cancers, autoimmune diseases, neurodegenerative disease, cardiovascular disease and pathogenic diseases. In another embodiment, the disease is solid cancers.

According to another aspect, the present disclosure provides a method for preparing the compound according to formula (I)-(V).

Described herein are $^{18}$F-prosthetic groups and methods for producing the $^{18}$F-prosthetic groups. Also described herein are radiolabeled compositions containing the $^{18}$F-prosthetic groups and the use of these radiolabeled compositions to diagnose, localize, monitor and/or assess diseased cells and/or tissues, and related biological conditions.

In order that the present description may be more readily understood, certain terms are first defined. Additional definitions are set forth throughout the detailed description. Unless defined otherwise, all technical and scientific terms used herein have the same meaning as commonly understood by one of ordinary skill in the art, and conventional methods of mass spectroscopy, NMR, HPLC, biochemistry, recombinant DNA techniques and pharmacology are employed.

As used herein, the singular forms "a", "an" and "the" include plural referents unless the context clearly dictates otherwise. The use of "or" or "and" means "and/or" unless stated otherwise. Furthermore, use of the term "including" as well as other forms, such as "include", "includes", and "included", is not limiting.

As used herein, "about" means within plus or minus ten percent of a number. For example, "about 100" would refer to any number between 90 and 110.

As used herein, "medical imaging" refers to the techniques and processes used to create images of the subject's body (or parts thereof) for clinical purposes (medical procedures seeking to reveal, diagnose or monitor disease) or medical science (including the study of normal anatomy and physiology).

As used herein, "positron emission tomography" or "PET" refers to a non-invasive, nuclear medicine technique that produces a three-dimensional image of tracer location in the body. The method detects pairs of gamma rays emitted indirectly by a positron-emitting radionuclide (tracer), which is introduced into the body on a biologically active molecule. PET imaging tools have a wide variety of uses and aid in drug development both preclinically and clinically. Exemplary applications include direct visualization of in vivo saturation of targets; monitoring uptake in normal tissues to anticipate toxicity or patient to patient variation; quantifying diseased tissue; tumor metastasis; and monitoring drug efficacy over time, or resistance over time.

The term "bioorthogonal chemistry" refers to any chemical reaction that can occur inside of living systems without interfering with native biochemical processes. The term includes chemical reactions that are chemical reactions that occur in vitro at physiological pH in, or in the presence of water. To be considered bioorthogonol, the reactions are selective and avoid side-reactions with other functional groups found in the starting compounds. In addition, the resulting covalent bond between the reaction partners should be strong and chemically inert to biological reactions and should not affect the biological activity of the desired molecule.

The term "click chemistry" refers to a set of reliable and selective bioorthogonal reactions for the rapid synthesis of new compounds and combinatorial libraries. Properties of for click reactions include modularity, wideness in scope, high yielding, stereospecificity and simple product isolation (separation from inert by-products by non-chromatographic methods) to produce compounds that are stable under physiological conditions. In radiochemistry and radiopharmacy, click chemisty is a generic term for a set of labeling reactions which make use of selective and modular building blocks and enable chemoselective ligations to radiolabel biologically relevant compounds in the absence of catalysts. A "click reaction" can be with copper, or it can be a copper-free click reaction.

The term "prosthetic group" or "bifunctional labeling agent" refers to a small organic molecule containing a radionuclide (e.g., $^{18}F$) that is capable of being linked to a millamolecule.

As used herein, "target" as a general reference to a "biological target" refers to a cell, tissue (e.g., cancer or tumor), a pathogenic microorganism (e.g., bacteria, virus, fungus, plant, prion, protozoa or portion thereof) or other molecule associated with a biological pathway, or a biological phenomenon, such as tissue inflammation, plaque formation, etc.

The term "targeting ligand", "targeting agent" or "targeting molecule" are used interchangeably to refer to a molecule, such as a peptide, millamolecule, etc., that binds to another molecule. In certain embodiments, a targeting agent is bound to the $^{18}F$-prosthetic group in order to "target" a molecule associated with a particular cell, tissue, pathogen or biological pathway.

The terms "specifically binds," ""specific binding," "selective binding, and "selectively binds," as used interchangeably herein refers to an peptide or polypeptide that exhibits affinity for a biological target, but does not significantly bind (e.g., less than about 10% binding) to a other molecules as measured by a technique available in the art such as, but not limited to, Scatchard analysis and/or competitive binding assays (e.g., competition ELISA, BIACORE assay).

The term "$IC_{50}$", as used herein, refers to the concentration of an $^{18}F$-radiolabeled-millamolecule based probe that inhibits a response, either in an in vitro or an in vivo assay, to a level that is 50% of the maximal inhibitory response, i.e., halfway between the maximal inhibitory response and the untreated response.

As used herein, the term "linked" refers to the association of two or more molecules. The linkage can be covalent or non-covalent.

The terms "diagnosis" or "detection" can be used interchangeably. Whereas diagnosis usually refers to defining a tissue's specific histological status, detection recognizes and locates a tissue, lesion or organism containing a particular detectable target.

The term "detectable" refers to the ability to detect a signal over the background signal. The term "detectable signal" as used herein in the context of imaging agents and diagnostics, is a signal derived from non-invasive imaging techniques such as, but not limited to, positron emission tomography (PET). The detectable signal is detectable and distinguishable from other background signals that may be generated from the subject. In other words, there is a measurable and statistically significant difference (e.g., a statistically significant difference is enough of a difference to distinguish among the detectable signal and the background, such as about 0.1%, 1%, 3%, 5%, 10%, 15%, 20%, 25%, 30%, or 40% or more difference between the detectable signal and the background) between the detectable signal and the background. Standards and/or calibration curves can be used to determine the relative intensity of the detectable signal and/or the background.

A "detectably effective amount" of a composition comprising an imaging agent described herein is defined as an amount sufficient to yield an acceptable image using equipment that is available for clinical use. A detectably effective amount of an imaging agent provided herein may be administered in more than one injection. The detectably effective amount can vary according to factors such as the degree of susceptibility of the individual, the age, sex, and weight of the individual, idiosyncratic responses of the individual, and the like. Detectably effective amounts of imaging compositions can also vary according to instrument and methodologies used. Optimization of such factors is well within the level of skill in the art.

As used herein, "administering," as used in the context of imaging agents refers to the physical introduction of a composition comprising an imaging agent to a subject, using any of the various methods and delivery systems known to those skilled in the art. Preferred routes of administration for the imaging agents described herein include intravenous, intraperitoneal, intramuscular, subcutaneous, spinal or other parenteral routes of administration, for example by injection or infusion. The phrase "parenteral administration" as used herein means modes of administration other than enteral and topical administration, usually by injection, and includes, without limitation, intravenous, intraperitoneal, intramuscular, intraarterial, intrathecal, intralymphatic, intralesional, intracapsular, intraorbital, intracardiac, intradermal, transtracheal, subcutaneous, subcuticular, intraarticular, subcapsular, subarachnoid, intraspinal, epidural and intrasternal injection and infusion, as well as in vivo electroporation. Alternatively, an imaging agent described herein can be administered via a non-parenteral route, such as a topical, epidermal or mucosal route of administration, for example, intranasally, orally, vaginally, rectally, sublingually or topically. Administering can also be performed, for example, once, a plurality of times, and/or over one or more extended periods.

The terms "co-administration" or the like, as used herein, are meant to encompass administration of the selected pharmaceutical agents to a single patient, and are intended to include regimens in which the agents are administered by the same or different route of administration or at the same or different time.

The terms "patient" and "subject" refer to any human or non-human animal that receives a composition comprising an imaging agent described herein. For in vitro applications, such as in vitro diagnostic and research applications, body fluids and cell samples of the above subjects will be suitable for use, such as blood, urine, or tissue samples.

The term "sample" can refer to a tissue sample, cell sample, a fluid sample, and the like. The sample may be taken from a subject. The tissue sample can include hair (including roots), buccal swabs, blood, saliva, semen, muscle, or from any internal organs. The fluid may be, but is not limited to, urine, blood, ascites, pleural fluid, spinal fluid, and the like. The body tissue can include, but is not limited to, skin, muscle, endometrial, uterine, and cervical tissue.

The term "isotopically pure" means that the element, compound, or composition contains a greater proportion of one isotope in relation to other isotopes. In certain embodiments, the element, compound, or composition is greater than about 40%, 50%, or 60% isotopically pure.

As used herein, a labeled molecule is "purified" when the labeled molecule is partially or wholly separated from unlabeled molecules, so that the fraction of labeled molecules is enriched compared to the starting mixture. A "purified" labeled molecule may comprise a mixture of labeled and unlabeled molecules in almost any ratio, including but not limited to about 5:95; 10:90; 15:85; 20:80; 25:75; 30:70; 40:60; 50:50; 60:40; 70:30; 75:25; 80:20; 85:15; 90:10; 95:5; 97:3; 98:2; 99:1 or 100:0.

The group "OTf" refers to triflate having the formula $CF_3SO_3$ or trifluoromethanesulfate.

The term "halo" or, alternatively, "halogen" or "halide" means fluoro, chloro, bromo or iodo.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

Various aspects described herein are described in further detail in the following subsections.

$^{18}F$ Radiolabeled Prosthetic Groups

In one aspect, provided herein is a PEGylated $^{18}F$-pyridine covalently bound to an azide with the following structure,

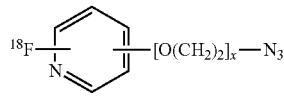

or a pharmaceutically acceptable salt thereof, wherein x is an integer from 1 to 8. In some embodiments, x is an integer from 2 to 6. In some embodiments x is an integer from 3 to 5. In some embodiments, x is 4. In related embodiments, $^{18}F$ is attached to the pyridine ortho to the N atom. In some embodiments, the $[O(CH_2)_2]_x$ moiety is present in the 1-3 configuration relative to the nitrogen on the pyridine ring. In some embodiments, the $[O(CH_2)_2]_x$ moiety is present in the 1-2 configuration relative to the nitrogen on the pyridine ring. In other embodiments, the $[O(CH_2)_2]_x$ moiety is present in the 1-4 configuration relative to the nitrogen on the pyridine ring.

In some embodiments, the $^{18}F$-radiolabeled compound has the structure

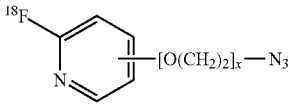

or a pharmaceutically acceptable salt thereof, wherein x is an integer from 1 to 8. In some embodiments, x is an integer from 2 to 6. In some embodiments x is an integer from 3 to 5. In some embodiments, x is 4. In some embodiments, the $[O(CH_2)_2]_x$ moiety is present in the 1-3 configuration relative to the nitrogen on the pyridine ring. In some embodiments, the $[O(CH_2)_2]_x$ moiety is present in the 1-2 configuration relative to the nitrogen on the pyridine ring. In other embodiments, the $[O(CH_2)_2]_x$ moiety is present in the 1-4 configuration relative to the nitrogen on the pyridine ring.

In some embodiments, the $^{18}F$-radiolabeled compound has the structure

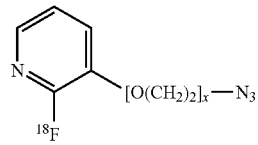

wherein x is an integer from 1 to 8. In some embodiments, x is an integer from 2 to 6. In some embodiments x is an integer from 3 to 5. In some embodiments, x is 4.

In some embodiments, the $^{18}F$-radiolabeled compound is [$^{18}F$]-3-(2-(2-(2-(2-azidoethoxy)ethoxy)ethoxy)ethoxy)-2-fluoropyridine ($^{18}F$-FPPEGA) and has the structure

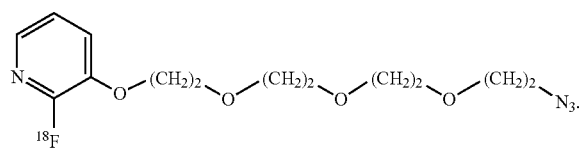

In alternative embodiments, the $^{18}$F-radiolabeled prosthetic group may contain additional groups on the pyridine ring which do not interfere with the fluorination reaction. In certain embodiments, additions to the pyridine ring include $C_{1-6}$ alkyl groups, for example methyl, ethyl and propyl.

In still other embodiments, the $^{18}$F-radiolabeled prosthetic group is a fused ring system with the following structure:

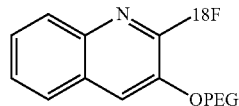

wherein "OPEG" is $[O(CH_2)_2]_x$, and x is an integer from 1 to 8. In some embodiments, x is an integer from 2 to 6. In some embodiments x is an integer from 3 to 5. In some embodiments, x is 4.

In a related aspect, provided herein is a method of preparing a PEGylated $^{18}$F-pyridine covalently bound to an azide with the following structure,

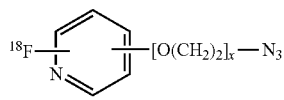

wherein x is an integer from 1 to 8, the method comprising the steps of (a) providing a solution of a compound a with the following structure:

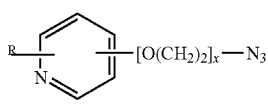

a wherein x is an integer from 1 to 8, and R is $NO_2$, Br, F or

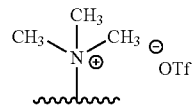

and is ortho to the N atom of the pyridine ring;

(b) providing a mixture of $^{18}$F in $^{18}$O water, 4,7,13,16,21,24-hexaoxa-1,10-diazabicyclo[8.8.8]hexacosane and a weak base;

(c) drying the mixture from step (b) to form a solid; and (d) reacting the solution from step (a) with the solid from step (c) to form the $^{18}$F-labeled compound.

In certain embodiments, the method produces a $^{18}$F-pyridine prosthetic group with the following structure b

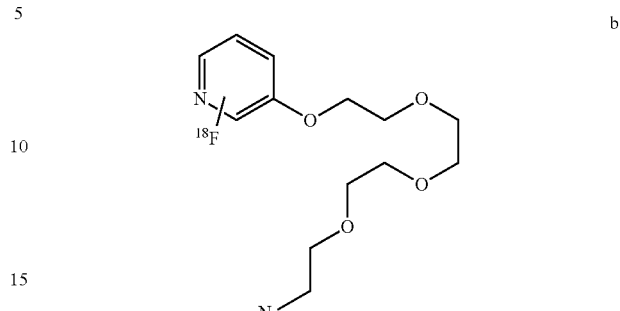

b (where $^{18}$F is ortho to the N atom), and includes the steps of (a) providing a solution of the compound of the structure

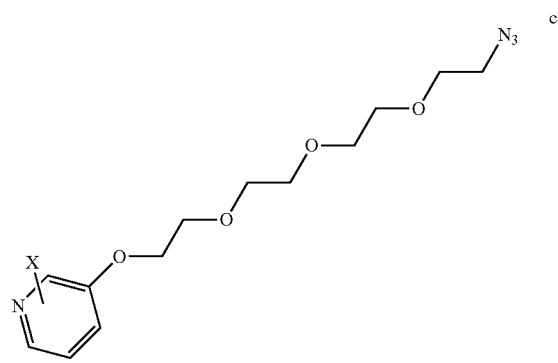

c (where X is ortho to the N atom) where X is $NO_2$, Br or

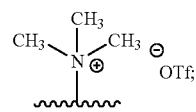

(b) providing a mixture of $^{18}$F in $^{18}$O water, 4,7,13,16,21,24-hexaoxa-1,10-diazabicyclo[8.8.8]hexacosane and weak base, such as $K_2CO_3$;

(c) drying the mixture from step (b) to form a solid; and (d) reacting the solution from step (a) with the solid from step (c) to form the $^{18}$F-labeled compound.

In certain embodiments, the method further comprises the step of producing a compound with the following structure a

In certain embodiments, the method comprises producing the $^{18}$F-pyridine prosthetic group [$^{18}$F]-3-(2-(2-(2-(2-azidoethoxy)ethoxy)ethoxy)ethoxy)-2-fluoropyridine

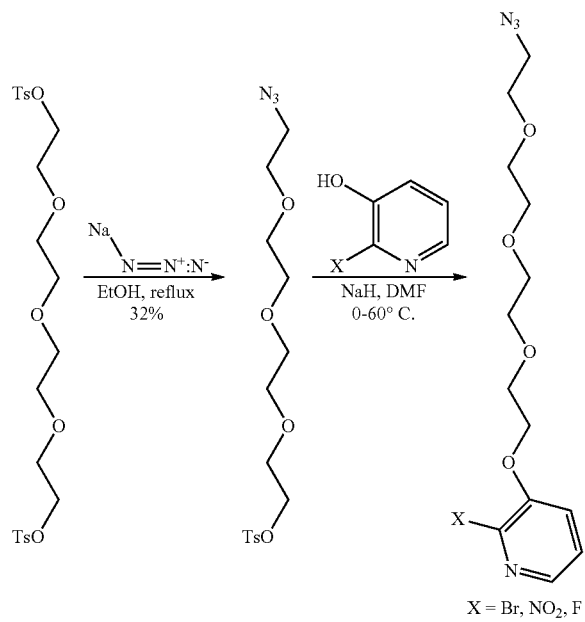

($^{18}$F-FPPEGA), e, from d, according to the following reaction conditions:

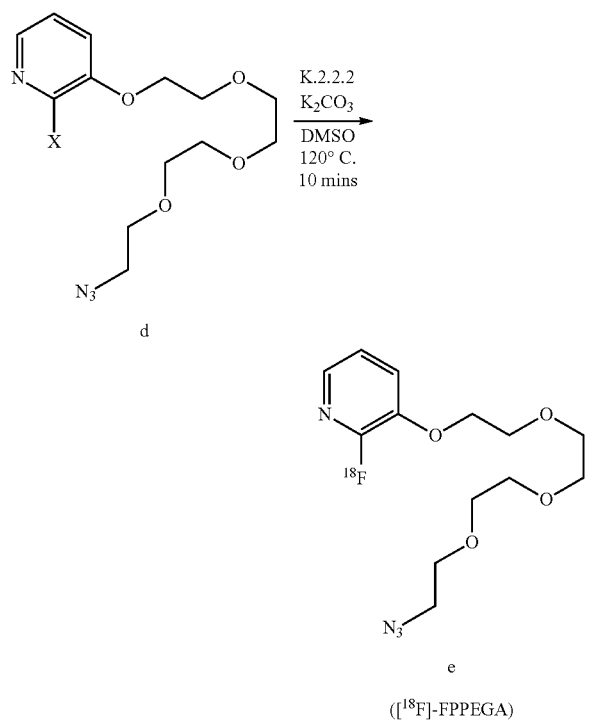

Formulations

Further provided are compositions, e.g., a pharmaceutical compositions, containing one or a combination of $^{18}$F-labeled targeting agents, described herein, formulated together with a pharmaceutically acceptable carrier. Such compositions may include one or a combination of (e.g., two or more different) agents described herein. For example, a pharmaceutical composition described herein can comprise a combination of $^{18}$F-labeled targeting agent and a drug.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, $^{18}$F-labeled targeting agent may be coated in a material to protect the compound from the action of acids and other natural conditions that may inactivate the compound.

The pharmaceutical compounds described herein may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition described herein also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions described herein include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions described herein is contemplated. Supplementary active compounds can also be incorporated into the compositions.

Pharmaceutical compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the $^{18}$F-labeled targeting agent in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of $^{18}$F-labeled targeting agent which can be combined with a carrier material to produce a single dosage form will vary depending upon the subject being treated, and the particular mode of administration. The amount of $^{18}$F-labeled targeting agent which can be combined with a carrier material to produce a single dosage form will generally be that amount of the composition which produces a detectable effect. Generally, out of one hundred per cent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Administration and Imaging

The $^{18}$F-labeled targeting agents described herein are useful in a variety of in vivo imaging applications (e.g., for tissue or whole body imaging). In certain embodiments, the $^{18}$F-labeled targeting agent can be used to image target-positive cells or tissues, e.g., target expressing tumors. For example, the labeled $^{18}$F-labeled targeting agent is administered to a subject in an amount sufficient to uptake the $^{18}$F-labeled targeting agent into the tissue of interest. The subject is then imaged using an imaging system such as PET for an amount of time appropriate for the $^{18}$F radionuclide. The $^{18}$F-labeled targeting agent-bound to cells or tissues expressing the targeting agent are then detected by the imaging system.

Typically, for imaging purposes it is desirable to provide the recipient with a dosage of millamolecule that is in the range of from about 1 mg to 200 mg as a single intravenous infusion, although a lower or higher dosage also may be administered as circumstances dictate. Typically, it is desirable to provide the recipient with a dosage that is in the range of from about 1 mg to 10 mg per square meter of body surface area of the protein or peptide for the typical adult, although a lower or higher dosage also may be administered as circumstances dictate. Examples of dosages proteins or peptides that may be administered to a human subject for imaging purposes are about 1 to 200 mg, about 1 to 70 mg, about 1 to 20 mg, and about 1 to 10 mg, although higher or lower doses may be used.

In certain embodiments, administration occurs in an amount of $^{18}$F-radiolabeled -millamolecule of between about 0.005 µg/kg of body weight to about 50 µg/kg of body weight per day, usually between 0.02 µg/kg of body weight to about 3 µg/kg of body weight. The mass associated with a PET tracer is in the form of the natural isotope, namely $^{19}$F for the $^{18}$F PET tracer. A particular analytical dosage for the instant composition includes from about 0.5 µg to about 100 µg of an $^{18}$F-radiolabeled millamolecule. The dosage will usually be from about 1 µg to about 50 µg of an $^{18}$F-radiolabeled millamolecule.

Dosage regimens are adjusted to provide the optimum detectable amount for obtaining a clear image of the tissue or cells which uptake the $^{18}$F-labeled targeting agent. It is especially advantageous to formulate parenteral compositions in dosage unit form for ease of administration and uniformity of dosage. Dosage unit form as used herein refers to physically discrete units suited as unitary dosages for the subjects to which the $^{18}$F-labeled targeting agent is to be administered. The specification for the dosage unit forms described herein are dictated by and directly dependent on (a) the unique characteristics of the targeting portion of the $^{18}$F-labeled targeting agent; (b) the tissue or cells to be targeted; (c) the limitations inherent in the imaging technology used.

For administration of the $^{18}$F-labeled targeting agent, the dosage used will depend upon the disease type, targeting compound used, the age, physical condition, and gender of the subject, the degree of the disease, the site to be examined, and others. In particular, sufficient care has to be taken about exposure doses to a subject. Preferably, a saturating dose of $^{18}$F is administered to the patient. For example, the amount of radioactivity of $^{18}$F-labeled targeting agent usually ranges from 3.7 megabecquerels to 3.7 gigabecquerels, and preferably from 18 megabecquerels to 740 megabecquerels. Alternatively, the dosage may be measured by millicuries, for example. In some embodiments, the amount of $^{18}$F imaging administered for imaging studies is 5 to 10 mCi. In other embodiments, an effective amount will be the amount of compound sufficient to produce emissions in the range of from about 1-5 mCi.

Actual dosage levels of the active ingredients in the pharmaceutical compositions described herein may be varied so as to obtain an amount of the active ingredient which is effective to achieve the desired uptake of the $^{18}$F-labeled targeting agent in the cells or tissues of a particular patient, composition, and mode of administration, without being toxic to the patient. It will be understood, however, that the total daily usage of the $^{18}$F-labeled targeting agent of the present disclosure will be decided by the attending physician or other attending professional within the scope of sound medical judgment. The specific effective dose level for any particular subject will depend upon a variety of factors, including for example, the activity of the specific composition employed; the specific composition employed; the age, body weight, general health, sex, and diet of the host; the time of administration; the route of administration; the rate of excretion of the specific compound employed; the duration of the treatment; other drugs, compounds and/or materials used in combination with the particular compositions employed, the age, sex, weight, condition, general health and prior medical history of the patient being treated, and like factors well known in the medical arts. In certain embodiments, the amount of $^{18}$F-radiolabeled probe administered into a human subject required for imaging will be determined by the prescribing physician with the dosage generally varying according to the quantity of emission from the $^{18}$F-radionuclide.

A composition described herein can be administered via one or more routes of administration using one or more of a variety of methods known in the art. As will be appreciated by the skilled artisan, the route and/or mode of administration will vary depending upon the desired results. Preferred routes of administration for $^{18}$F-labeled targeting agent described herein include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. In certain embodiments, $^{18}$F-radiolabeled targeting compound is administered intravenously.

Alternatively, an $^{18}$F-labeled targeting agent described herein can be administered via a non-parenteral route, such as a topical, epidermal or mucosal route of administration, for example, intranasally, orally, vaginally, rectally, sublingually or topically.

In certain embodiments, the $^{18}$F-labeled targeting agent described herein can be formulated to ensure proper distribution in vivo. For example, the blood-brain barrier (BBB) excludes many highly hydrophilic compounds. Agents may cross the BBB by formulating them, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134); p120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994).

The following illustrative procedure may be utilized when performing PET imaging studies on patients in the clinic. The patient is premedicated with unlabeled millamolecule some time prior to the day of the experiment and is fasted for at least 12 hours allowing water intake ad libitum. A 20 G two-inch venous catheter is inserted into the contralateral ulnar vein for radiotracer administration concentration in the blood.

The patient is positioned in the PET camera and a tracer dose of the PET tracer of $^{18}$F-radiolabeled millamolecule (<20 mCi) is administered via i.v. catheter. Either arterial or venous blood samples are taken at appropriate time intervals throughout the PET scan in order to analyze and quantitate the fraction of unmetabolized PET tracer of [$^{18}$F] Example 2 compound in plasma. Images are acquired for up to 120 min. Within ten minutes of the injection of radiotracer and at the end of the imaging session, 1 ml blood samples are obtained for determining the plasma concentration of any unlabeled millamolecule which may have been administered before the PET tracer.

Tomographic images are obtained through image reconstruction. For determining the distribution of radiotracer, regions of interest (ROIs) are drawn on the reconstructed image including, but not limited to, the lungs, liver, heart, kidney, skin or other organs and tissue. Radiotracer uptakes over time in these regions are used to generate time activity curves (TAC) obtained in the absence of any intervention or in the presence of the unlabeled millamolecule at the various dosing paradigms examined. Data are expressed as radioactivity per unit time per unit volume (μCi/cc/mCi injected dose). TAC data are processed with various methods well-known in the field to yield quantitative parameters, such as Binding Potential (BP) or Volume of Distribution ($V_T$), that are proportional to the density of unoccupied target positive tissue.

Kits and Articles of Manufacture

Also provided are kits for producing the $^{18}$F-radiolabeled targeting compositions described herein and instructions for use. Kits typically include a packaged combination of reagents in predetermined amounts with instructions and a label indicating the intended use of the contents of the kit. The term label includes any writing, or recorded material supplied on or with the kit, or which otherwise accompanies the kit.

For example, in some embodiments, the kit contains the reagents necessary for the prosthetic group in condition to be fluorinated on site with $^{18}$F, and then linking the radiolabeled prosthetic group to the targeting molecule (e.g., millamolecule prior to administration.

In certain embodiments, a kit comprises one or more reagents necessary for forming an $^{18}$F labeled anti-PD-L1 millamolecule in vivo imaging agent, such as that described herein. For example, a kit may comprise a first vial comprising anti-PD-L1 millamolecule and a second vial comprising [$^{18}$F]FPPEGA. A kit may comprise a first vial comprising anti-PD-L1 millamolecule, a second vial comprising 4-PEG-tosyl-azide and a third vial comprising $^{18}$F in $O^{18}$ water. The kits may further comprise vials, solutions and optionally additional reagents necessary for the manufacture of PD-L1 millamolecule-PEG4-DBCO-$^{18}$F.

In some embodiments, the kit can further contain at least one additional reagent (e.g., pharmaceutically acceptable carrier). In some embodiments, the kit includes the reaction precursors to be used to generate the labeled probe according to the methods disclosed herein. The components of the kit can be tailored to the particular biological condition to be monitored as described herein. The kit can further include appropriate buffers and reagents known in the art for administering various combinations of the components listed above to the host cell or host organism. The imaging agent and carrier may be provided in solution or in lyophilized form. When the imaging agent and carrier of the kit are in lyophilized form, the kit may optionally contain a sterile and physiologically acceptable reconstitution medium such as water, saline, buffered saline, and the like. Suitable containers include, for example, bottles, vials, syringes, and test tubes. The containers may be formed from a variety of materials such as glass or plastic. It may further include other materials desirable from a commercial and user standpoint, including other buffers, diluents, filters, needles, syringes, and package inserts with instructions for use.

Uses

Methods of imaging using $^{18}$F-labeled targeting agents are provided herein. Positron emission tomography (PET) tracers such as the present $^{18}$F-radiolabeled millamolecule-based PET probes can be used with currently available PET technology for use in exploratory and diagnostic imaging applications in vitro and in vivo. Imaging techniques and equipment for $^{18}$F imaging by PET scanning are well known in the art (see, e.g., U.S. Pat. Nos. 6,358,489; 6,953,567; Page et al., Nuclear Medicine And Biology, 21:911-919, 1994; Choi et al., Cancer Research 55:5323-5329, 1995; Zalutsky et al., J. Nuclear Med., 33:575-582, 1992) and any such known PET imaging technique or apparatus may be utilized.

In vivo applications of the imaging methods provided herein include disease diagnosis, monitoring of disease progression, prognosis, determining likelihood of a subject to respond to a treatment, determining eligibility to a treatment, monitoring of clinical response to therapy, clinical evaluation and dose selection of therapeutic compounds, preclinical studies of potential drug candidates in animal models, and the study of regional distribution and concentration of target molecules in tissues and organs. In vitro applications include screening of drug candidates in cell assays (e.g., competition assays, affinity assays, etc.).

In some embodiments, the $^{18}$F-labeled targeting agents can be used to determine the relationship between level of tissue occupancy by candidate therapeutic compounds and clinical efficacy in patients; to determine dose selection for clinical trials of drug candidates prior to initiation of long term clinical studies; and to compare potencies of different drug candidates.

In some embodiments, the $^{18}$F-radiolabeled targeting compound is used in a method for in in vivo imaging normal or diseased tissues and/or organs (e.g., lungs, heart, kidneys, liver, and skin). For example, the $^{18}$F-radiolabeled targeting compound is administered to a subject in an amount effective to result in uptake of the $^{18}$F-radiolabeled targeting compound into the cells or tissue of interest. The subject is then introduced to an appropriate imaging system (e.g., PET system) for a sufficient amount of time to allow detection of the $^{18}$F-radiolabeled targeting compound. The location of the detected signal from the $^{18}$F-radiolabeled targeting compound can be correlated with the location of the cells or tissue of interest. In some embodiments, the dimensions of the location can be determined as well. In vivo imaging is described herein. See also U.S. Pat. Nos. 6,126,916; 6,077, 499; 6,010,680; 5,776,095; 5,776,094; 5,776,093; 5,772, 981; 5,753,206; 5,746,996; 5,697,902; 5,328,679; 5,128, 119; 5,101,827; and 4,735,210, each incorporated herein by reference.

Accordingly, in certain aspects, provided is a method of obtaining an image of an $^{18}$F-radiolabeled millamolecule-based probe, the method comprising administering the $^{18}$F-radiolabeled millamolecule-based probe to a subject, and imaging in vivo the distribution of the $^{18}$F-radiolabeled millamolecule-based probe by PET.

In certain embodiments, the subject is a mammal, for example, a human, dog, cat, ape, monkey, rat, or mouse.

In certain aspects, provided is a method of diagnosing the presence of a disease in a subject, the method comprising administering to a subject in need thereof an $^{18}$F-radiolabeled millamolecule-based probe which binds to a target molecule associated with the presence of the disease, and obtaining a radio-image of at least a portion of the subject to detect the presence or absence of the $^{18}$F-radiolabeled millamolecule-based probe.

In some embodiments, the disease is a solid cancer, hematopoietic cancer, hematological cancer, autoimmune disease, neurodegenerative disease, cardiovascular disease or pathogenic infection.

PET imaging with an $^8$F-radiolabeled targeting compound may be used to qualitatively or quantitatively detect the targeting compound. An $^8$F-radiolabeled targeting compound imaging agent may be used as a biomarker, and the presence or absence of a positive signal in a subject may be indicative that, e.g., the subject would be responsive to a given therapy, e.g., a cancer therapy, or that the subject is responding or not to a therapy.

In some embodiments, the steps of this method can be repeated at determined intervals so that the location and/or size of the disease can be monitored as a function of time and/or treatment. In certain embodiments, the $^{18}$F-radiolabeled targeting compound can be used in a subject undergoing treatment (e.g., chemotherapy, etc.), to aid in visualizing response to the treatment. For example, the $^{18}$F-radiolabeled targeting compound is typically visualized and sized prior to treatment, and periodically (e.g., daily, weekly, monthly, intervals in between these, and the like) during treatment to monitor the progression or regression of the disease in the patient.

Accordingly, in certain aspects, provided is a method of monitoring the progress of a disease in a subject in need thereof, the method comprising administering to the subject an $^{18}$F-radiolabeled millamolecule-based probe which binds to a target molecule associated with the presence of the disease at a first time point and obtaining an image of at least a portion of the subject to determine the amount of diseased cells or tissue, and administering to the subject the $^{18}$F-radiolabeled millamolecule-based probe at one or more subsequent time points and obtaining an image of at least a portion of the subject at each subsequent time point (e.g., same portion as the first time point).

In certain embodiments, the size of a tumor can be monitored in a subject undergoing cancer therapy (e.g., chemotherapy, radiotherapy) and the extent of regression of the tumor can be monitored in real-time based on detection of $^{18}$F-radiolabeled tumor targeting.

In some embodiments, the methods herein are used to evaluate the patient's response to therapy. In some embodiments, the methods are used to select or modify the dosage of therapeutic compounds. In some embodiments, the methods are used to monitor the uptake of the $^{18}$F-radiolabeled targeting compound in normal tissues to analyze toxicity or patient to patient variation. In some embodiments, the methods are used to monitor drug efficacy or to detect drug resistance.

In some embodiments, the radiolabeled compounds are administered to mammals, preferably humans, in a pharmaceutical composition, either alone or in combination with pharmaceutically acceptable carriers or diluents according to standard pharmaceutical practice. Such compositions can be administered orally or parenterally, including the intravenous, intramuscular, intraperitoneal, subcutaneous, rectal and topical routes of administration. In certain embodiments, administration is intravenous. In certain embodiments the radiolabeled compound is administered via intravenous injection within less than one hour of synthesis.

In some embodiments, the biological activity of the $^{18}$F-radiolabeled targeting agent in vivo may be measured in terms of organ-specific uptake by biodistribution studies and dynamic small animal PET imaging studies in an appropriate animal model. For example, for biodistribution studies, a group of animals are injected with the $^{18}$F-radiolabeled targeting agent and the subsets of the animals are sacrificed at one or more time intervals (e.g., 5 min., 10 min., 30 min., 60 min., 2 h). Organs and tissues of interest are rapidly excised and weighed, and radioactivity determined. Accumulated radioactivity in organs and selected tissues is calculated as the percentage of injected dose (%ID).

In some embodiments, the $^{18}$F-radiolabeled targeting agent provided herein is used in vitro as a screening tool to select compounds for use in treating tissues or cells. For example, in some embodiments, diseased cells are incubated with the $^{18}$F-radiolabeled targeting compound during or after exposure to one or more candidate drugs. The ability of the drug candidate to affect the disease can be imaged over time using the $^{18}$F-radiolabeled targeting compound.

For example, the integrity of biological activity of the $^{18}$F-radiolabeled targeting agent in vitro in terms of specific binding to the selected target molecule and uptake of the radiolabeled composition is assessed in a cell line expressing the target molecule. For binding and cell association assays, cells are incubated at 4° C. or 37° C. for an appropriate time with the $^{18}$F-radiolabeled targeting composition. Nonspecific binding is determined by the addition of an excess of unlabeled targeting agent. The extent of specific binding is calculated by subtracting the nonspecific binding from the total binding. Uptake is expressed as a percentage of the total added dose of targeting agent to the cells per microgram of protein (% ID/µg cell protein).

In a related aspect, the present invention provides a diagnostic or radiopharmaceutical composition for in vivo or in vitro, which includes an $^{18}$F-radiolabeled millamolecule-based probe, and a pharmaceutically acceptable carrier.

INCORPORATION BY REFERENCE

All documents and references, including patent documents and websites, described herein are individually incorporated by reference to into this document to the same extent as if there were written in this document in full or in part.

The disclosure is now described by reference to the following examples, which are illustrative only, and are not intended to limit the present disclosure. While the disclosure has been described in detail and with reference to specific embodiments thereof, it will be apparent to one of skill in the art that various changes and modifications can be made thereto without departing from the spirit and scope thereof.

Analysis Condition A:
    Column: Waters BEH C18, 2.0×50 mm, 1.7-µm particles; Mobile Phase A: 5:95 acetonitrile:water with 10 mM ammonium acetate; Mobile Phase B: 95:5 acetonitrile: water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm.

Analysis Condition B:
    Column: Waters BEH C18, 2.0×50 mm, 1.7-µm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm.

Single-Coupling Procedure:
    To the reaction vessel containing resin from the previous step was added piperidine:DMF (20:80 v/v, 5.0 mL). The mixture was periodically agitated for 3 or 5 min. and then the solution was drained through the frit. To the reaction vessel was added piperidine:DMF (20:80 v/v, 5.0 mL). The mixture was periodically agitated for 3 or 5 min. and then the solution was drained through the frit. The resin was washed successively five times as follows: for each wash, DMF (4.0 mL) was added through the top of the vessel and the resulting mixture was periodically agitated for 60 seconds before the solution was drained through the frit. To the reaction vessel was added the amino acid (0.2M in DMF, 5.0 mL, 10 eq), then HATU or HCTU (0.2M in DMF, 5.0 mL, 10 eq), and finally NMM (0.8M in DMF, 2.5 mL, 20 eq). The mixture was periodically agitated for 60 min., then the reaction solution was drained through the frit. The resin was washed successively four times as follows: for each wash, DMF (4.0 mL) was added through the top of the vessel and the resulting mixture was periodically agitated for 30 seconds before the solution was drained through the frit. To the reaction vessel was added a solution of acetic anhydride: DIEA:DMF (10:1:89 v/v/v, 5.0 mL). The mixture was periodically agitated for 10 min., then the solution was drained through the frit. The resin was washed successively four times as follows: for each wash, DMF (4.0 mL) was added through the top of the vessel and the resulting mixture was periodically agitated for 90 seconds before the solution was drained through the frit. The resulting resin was used directly in the next step.

Double-Coupling Procedure:
    To the reaction vessel containing resin from the previous step was added a solution of piperidine:DMF (20:80 v/v, 5.0 mL). The mixture was periodically agitated for 3 min. and then the solution was drained through the frit. To the reaction vessel was added a solution of piperidine:DMF (20:80 v/v, 5.0 mL). The mixture was periodically agitated for 3 min. and then the solution was drained through the frit. The resin was washed successively three times as follows: DMF (7 mL) wash from top, followed by DMF (7 mL) wash from bottom and finally with DMF (7 mL) wash from top. To the reaction vessel was added the amino acid (0.2M in DMF, 2.5 mL, 5 eq), HATU (0.5M in DMF, 1.0 mL, 5 eq), and DIPEA (2M in NMP, 0.5 mL, 10 eq). The mixture was mixed by $N_2$ bubbling for 5 min. at 75° C. for all amino acids, except Fmoc-Cys(Trt)-OH and Fmoc-His(Trt)-OH which are coupled at 50° C., the reaction solution was drained through the frit. The resin was washed successively three times as follows: DMF (7 mL) wash from top, followed by DMF (7 mL) wash from bottom and finally with DMF (7 mL) wash from top. To the reaction vessel was added the amino acid (0.2M in DMF,2.5 mL, 5 eq), HATU (0.5M in DMF, 1.0 mL, 5 eq), and DIPEA (2M in NMP, 0.5 mL, 10 eq). The mixture was mixed by N$_2$ bubbling for 5 min. at 75° C. for all amino acids, except Fmoc-Cys(Trt)-OH and Fmoc-His(Trt)-OH which are coupled at 50° C., the reaction solution was drained through the frit. The resin was washed successively three times as follows: DMF (7 mL) wash from top, followed by DMF (7 mL) wash from bottom and finally with DMF (7 mL) wash from top. To the reaction vessel was added a solution of acetic anhydride:DIEA:DMF (10:1:89 v/v/v, 5.0 mL). The mixture was periodically bubbled for 2 min. at 65° C., then the solution was drained through the frit. The resin was washed successively three times as follows: DMF (7 mL) wash from top, followed by DMF (7 mL) wash from bottom and finally with DMF (7 mL) wash from top. The resulting resin was used directly in the next step.

INTERMEDIATE 1300V

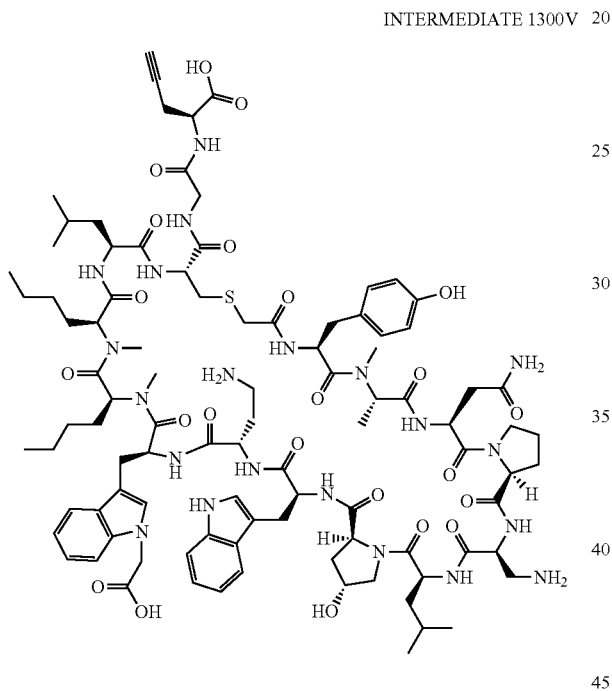

The following peptide was synthesized on a 1 mmol. The underlined steps employed the double-coupling procedure, and italicized residues were coupled with a 30 min single coupling. ClAc-Tyr-[N-Me]Ala-Asn-Pro-Dap-Leu-Hyp-Trp-Dab-[(S)-2-amino-3-(1-(carboxymethyl)-1H-indol-3-yl)propanoic acid]-[N—Me]Nle-Leu-Cys-Gly-[(S)-propargylglycine]; where the (S) propargylglycine was incorporated onto 2-chlorotrityl resin. After deprotection and cyclization according to the procedures above, the compound was purified as follows: The crude material was purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol: water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 16.4 mg, and its estimated purity by LCMS analysis was 96%. Analysis condition A: Retention time=1.49 min; ESI-MS(+) m/z 992.3 (M+2H), most abundant ion. Analysis condition B: Retention time=3.02 min; ESI-MS(+) m/z 992.3 (M+2H), most abundant ion; ESI-HRMS(+) m/z: Calculated: 991.9953 (M+2H)

Found: 991.9926 (M+2H).

Synthesis of [$^{18}$F]-3-(2-(2-(2-(2-azidoethoxy)ethoxy)ethoxy)ethoxy)-2-fluoropyridine

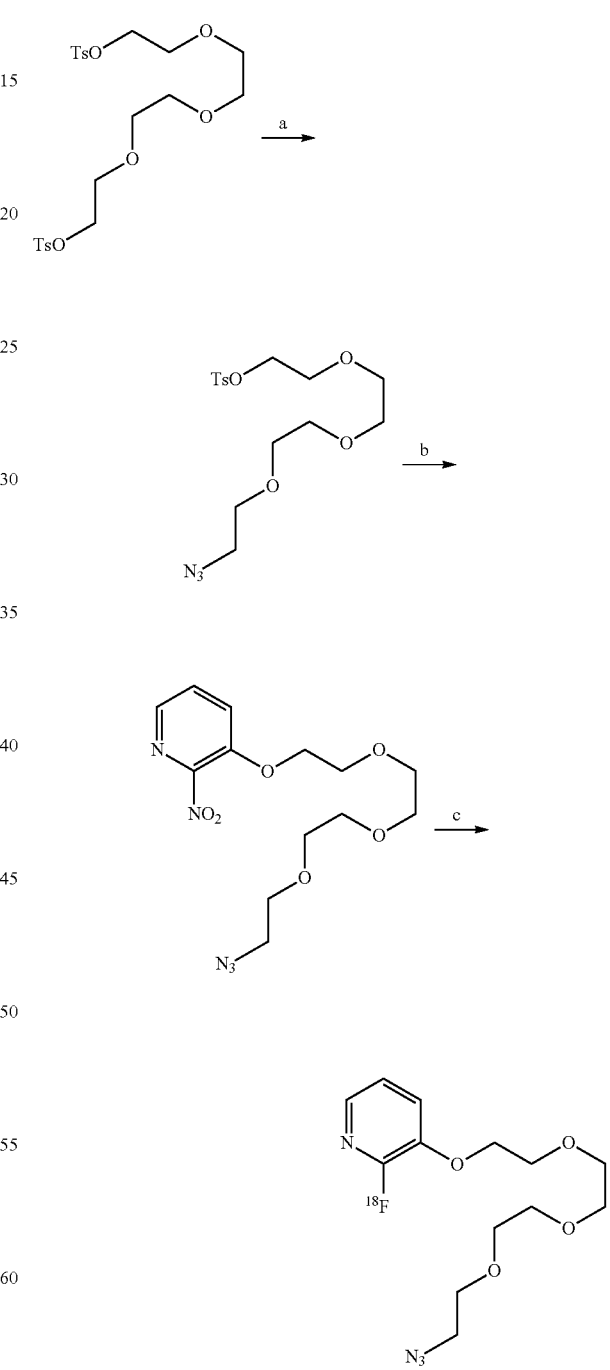

Regeants and Conditions: a) NaN$_3$, ethanol 90° C. 17 hrs; b) NaH, 2-nitropyridin-3-ol 0-60° C., 4 hrs; c) K.2.2.2 K[$^{18}$F], DMSO 120° C. 10 mins;

EXAMPLE 1

Preparation of 2-(2-(2-(2-azidoethoxy)ethoxy)ethoxy)ethyl 4-methylbenzenesulfonate

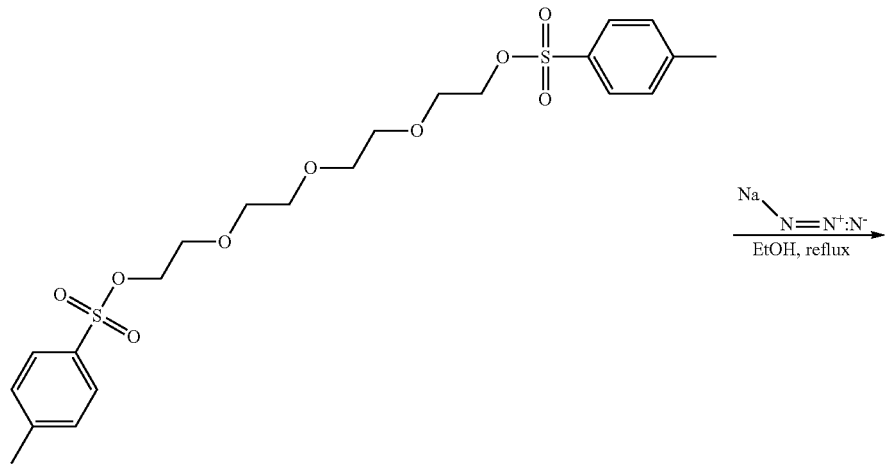

A mixture of ((oxybis(ethane-2,1-diyl))bis(oxy))bis(ethane-2,1-diyl) bis(4-methylbenzenesulfonate) (5 g, 9.95 mmol) and sodium azide (0.647 g, 9.95 mmol) were dissolved in ethanol (50 mL) and the reaction was refluxed at 90° C. over a 17 hour period. The solvent was removed using partial vacuum and then loaded onto a 40 gram silica cartridge and purified using flash chromatography (Isco-CombiFlash—eluted using a linear gradient method starting from 10% ethyl acetate in hexanes going to a 90% ethyl acetate in hexanes over a 45 minute period). The pooled fractions were checked by TLC and combined to give 2-(2-(2-(2-azidoethoxy)ethoxy)ethoxy)ethyl 4-methylbenzenesulfonate as a colorless oil. Due to the reactive nature of the 2-(2-(2-(2-azidoethoxy)ethoxy)ethoxy)ethyl 4-methylbenzenesulfonate product this material was used "as is" without any further characterizations.

EXAMPLE 2

Preparation of 3-(2-(2-(2-(2-azidoethoxy)ethoxy)ethoxy)ethoxy)-2-fluoropyridine

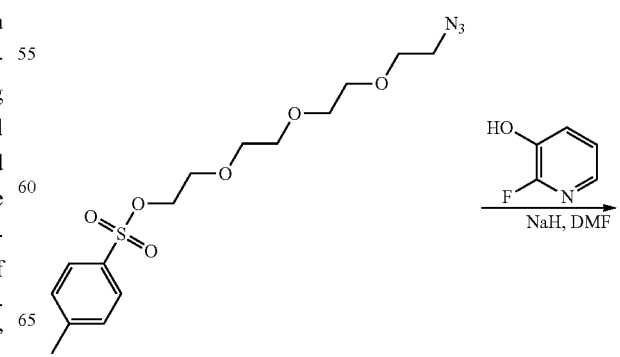

-continued

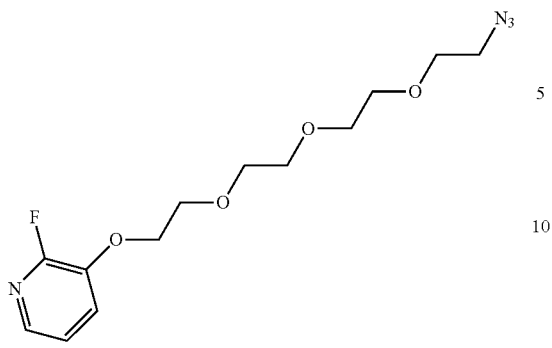

To a suspension of sodium hydride (0.129 g, 3.21 mmol) in DMF (10 mL) at 0° C. was dropwise added a stirring solution of 2-fluoropyridin-3-ol (0.363 g, 3.21 mmol) in DMF (5 mL), then followed by the dropwise addition of the solution of 2-(2-(2-(2-azidoethoxy)ethoxy)ethoxy)ethyl 4-methylbenzenesulfonate (1.00 g, 2.68 mmol) in DMF (5 mL). The suspension was held at 0° C. for 10 min, then brought to ambient temperature for 1 hour, followed by additional heating at 60° C. for 4 hours. The solvent was removed in vacuo. 100 ml of ethyl acetate was added followed by 3 separate wash extractions with concentrated brine solution. The organic layer was dried over sodium sulfate, filtered, and concentrated. The crude material was purified using flash chromatography (IscoCombiFlash—eluted with 10-50% EtOAc in Hex) to give a colorless oil. 3-(2-(2-(2-(2-azidoethoxy)ethoxy)ethoxy)ethoxy)-2-fluoropyridine (702 mg, 2.233 mmol, 83% yield) was isolated as a clear oil. $^1$H NMR (400 MHz, CHLOROFORM-d) δ 7.75 (dt, J=4.9, 1.6 Hz, 1H), 7.33 (ddd, J=10.0, 8.1, 1.5 Hz, 1H), 7.10 (ddd, J=7.9, 4.9, 0.7 Hz, 1H), 4.30-4.16 (m, 2H), 3.95-3.83 (m, 2H), 3.80-3.61 (m, 10H), 3.38 (t, J=5.1 Hz, 2H) 13C NMR (101 MHz, CHLOROFORM-d) d 142.3, 137.7, 137.5, 123.4, 123.4, 121.7, 121.6, 77.3, 76.7, 70.9, 70.7, 70.6, 70.0, 69.4, 69.0, 50.6 19F NMR (400 MHz, CHLOROFORM-d) δ −83.55. HRMS (ESI) Theory: C13H20FN4O4+ m/z 315.464; found 315.1463.

EXAMPLE 3

Preparation of 3-(2-(2-(2-(2-azidoethoxy)ethoxy)ethoxy)ethoxy)-2-nitropyridine

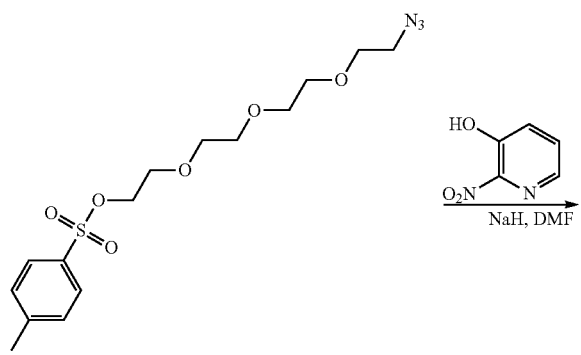

-continued

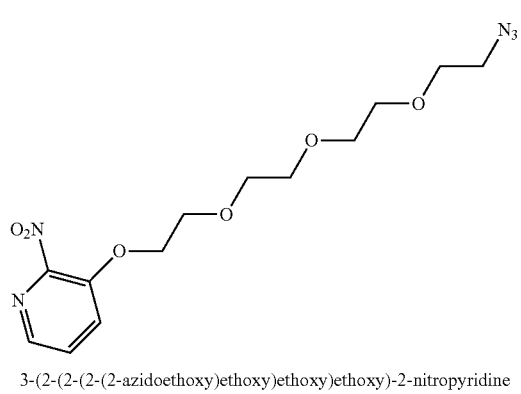

3-(2-(2-(2-(2-azidoethoxy)ethoxy)ethoxy)ethoxy)-2-nitropyridine

Sodium hydride (0.121 g, 3.01 mmol) (60% suspension in oil) was dissolved in DMF (7.0 mL) and the resulting suspension was cooled to 0° C. A solution of 2-nitropyridin-3-ol (0.384 g, 2.74 mmol) in DMF (1.5 mL) was added slowly, followed by the dropwise addition of 2-(2-(2-(2-azidoethoxy)ethoxy)ethoxy)ethyl 4-methylbenzenesulfonate (1.023 g, 2.74 mmol) in DMF (1.5 mL). The suspension was held at 0° C. for 10 minutes, then brought to ambient temperature for 2 hours followed by heating 60° C. for a 72 hour period. The reaction was quenched with 10 ml of DI water, followed by ethyl acetate extraction (3×10 mL). Pooled EtOAc extracts were washed with a concentrated brine solution (10 mL), dried over sodium sulfate, filtered, and evaporated under reduced pressure to give a light yellow oil. The crude was purified by flash chromatography. 24 g silica cartridge, 25 mL/min, starting from 10% ethyl acetate in hexanes, followed by a linear change to 50% ethyl acetate in hexanes over a 25 minute period. After this time, the gradient was held at this solvent composition for 10 minutes then changed to 100% ethyl acetate over a 10 minute period. 3-(2-(2-(2-(2-azidoethoxy)ethoxy)ethoxy)ethoxy)-2-nitropyridine was eluted between the 30-40 minute portion of the chromatogram and the pooled fractions were evaporated under reduced pressure, then under vacuum for 2 hours to give 3-(2-(2-(2-(2-azidoethoxy)ethoxy)ethoxy)ethoxy)-2-nitropyridine (687 mg, 1.973 mmol, 72.0% yield) as a light yellow oil. $^1$H NMR (400 MHz, CHLOROFORM-d) δ 8.11 (dt, J=4.9, 1.6 Hz, 1H), 7.60 (ddd, J=10.0, 8.1, 1.5 Hz, 1H), 7.52 (ddd, J=7.9, 4.9, 0.7 Hz, 1H), 4.30-4.16 (m, 2H), 3.95-3.83 (m, 2H), 3.80-3.61 (m, 10H), 3.38 (t, J=5.1 Hz, 2H) 13C NMR (101 MHz, CHLOROFORM-d) d 147.3, 139.5, 128.4, 124.4. 71.1, 70.7, 70.6, 70.0, 69.9, 69.3, 50.7. HRMS (ESI) Theory:C13H20N5O6+ m/z 342.1408; found 342.1409.

EXAMPLE 4

Synthesis of 3-(2-(2-(2-(2-azidoethoxy)ethoxy)ethoxy)ethoxy)-2-bromopyridine

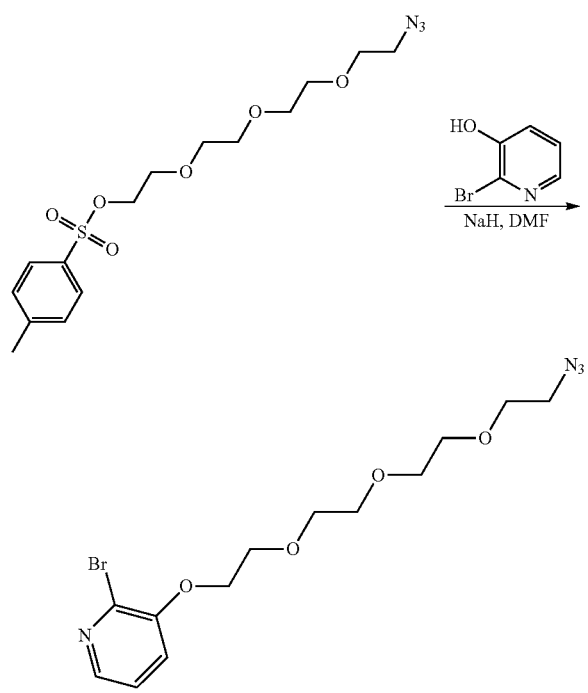

To the suspension of sodium hydride (NaH, 25.7 mg, 0.643 mmol) in dimethylformamide (DMF, 5 mL) at 0° C. was dropwise added a solution of 2-bromopyridin-3-ol (112 mg, 0.643 mmol) in DMF (1 mL), followed by the dropwise addition of the solution of 2-(2-(2-(2-azidoethoxy)ethoxy)ethoxy)ethyl 4-methylbenzenesulfonate (200 mg, 0.536 mmol) in DMF (1 mL). The suspension was held at 0° C. for 10 minutes, then brought to ambient temperature and held for 1 hour, followed by heating to 60° C. for 4 hours. Upon completion of heating, the solvent of the crude reaction mixture was removed in vacuo. The crude reaction was reconstituted in 50 mL of ethyl acetate, washed with 2×50 mL of a aqueous brine solution, and the organic layer was dried over magnesium sulfate, filtered, and concentrated in vacuo. The crude reaction was purified using reverse-phase HPLC to give3-(2-(2-(2-(2-azidoethoxy)ethoxy)ethoxy)ethoxy)-2-bromopyridine, TFA (112 mg, 0.229 mmol, 42.7% yield) as a light yellow oil. HRMS ESI m/z (M+H), Theory C13H20BrN4O4 375.0664 found 375.0662; $^1$H NMR (400 MHz, DMSO-$d_6$) δ 7.97 (dd, J=4.6, 1.5 Hz, 1H), 7.54 (dd, J=8.2, 1.6 Hz, 1H), 7.40 (dd, J=8.1, 4.6 Hz, 1H), 4.24 (dd, J=5.3, 3.9 Hz, 2H), 3.85-3.78 (m, 2H), 3.68-3.62 (m, 2H), 3.62-3.52 (m, 8H), 3.42-3.34 (m, 2H).

Synthesis of Trimethylanilium Compound

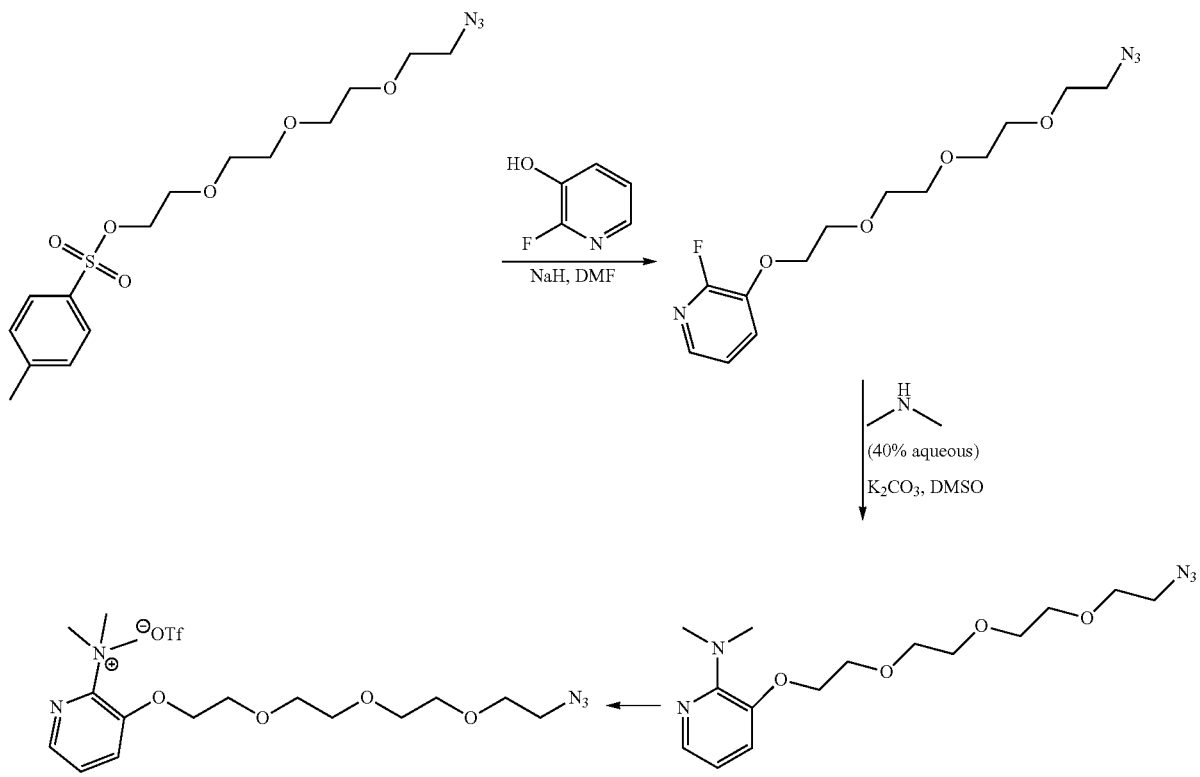

EXAMPLE 5

Synthesis of 3-(2-(2-(2-(2-azidoethoxy)ethoxy)ethoxy)ethoxy)-N,N-dimethylpyridin-2-amine

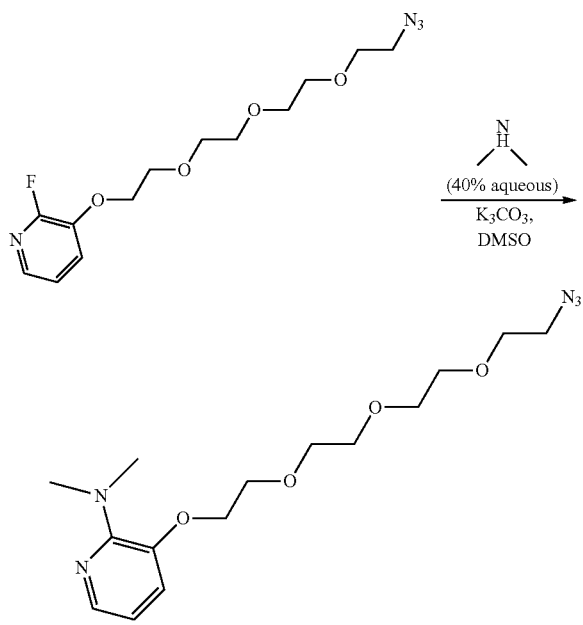

A mixture of 3-(2-(2-(2-(2-azidoethoxy)ethoxy)ethoxy)ethoxy)-2-fluoropyridine (160 mg, 0.509 mmol), potassium carbonate (K2CO3, 84 mg, 0.611 mmol), and dimethylamine (40% in water, 0.097 mL, 0.764 mmol) in dimethylsulfoxide (DMSO, 2.5 mL) were heated in a sealed pressure-proof vessel at 110° C. for 14 hours. Upon completion of heating, the solvent of the crude reaction mixture was removed in vacuo. The crude reaction was reconstituted in 50 mL of ethyl acetate, washed with 2×50 mL of a aqueous brine solution, and the organic layer was dried over magnesium sulfate, filtered, and concentrated in vacuo. The crude reaction was purified using normal-phase chromatography to give 3-(2-(2-(2-(2-azidoethoxy)ethoxy)ethoxy)ethoxy)-N,N-dimethylpyridin-2-amine (140 mg, 0.413 mmol, 81% yield) as a colorless oil. $^1$H NMR (400 MHz, CHLOROFORM-d) δ 7.86 (dd, J=4.9, 1.5 Hz, 1H), 7.02 (dd, J=7.8, 1.5 Hz, 1H), 6.73 (dd, J=7.8, 4.9 Hz, 1H), 4.20-4.07 (m, 2H), 3.98-3.86 (m, 2H), 3.81-3.61 (m, 9H), 3.38 (t, J=5.1 Hz, 2H), 3.13-2.94 (m, 6H), 1.69 (s, 2H). HRMS (ESI) Theory:C15H26N5O4+ m/z 340.1980; found 340.1979.

EXAMPLE 6

Synthesis of 3-(2-(2-(2-(2-azidoethoxy)ethoxy)ethoxy)ethoxy)-N,N,N-trimethylpyridin-2-aminium

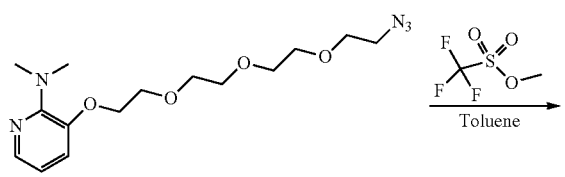

-continued

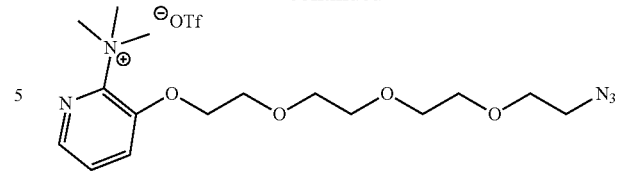

Methyl trifluoromethanesufonate (0.065 mL, 0.589 mmol) was added to the solution of 3-(2-(2-(2-(2-azidoethoxy)ethoxy)ethoxy)ethoxy)-N,N-dimethylpyridin-2-amine (40 mg, 0.118 mmol) in toluene (1.5 mL) in a sealed container under a steady stream of nitrogen. The reaction mixture was stirred at room temperature over a 14 hour period. The solvent was removed and the resultant residue was washed with 2×10 ml of ether, azeotropically dried with 2×1 ml of dichloromethane, and dried under high-pressure vacuum overnight to give 3-(2-(2-(2-(2-azidoethoxy)ethoxy)ethoxy)ethoxy)-N,N,N-trimethylpyridin-2-aminium, trifluoromethanesulfonate salt in quantitative yield as a thick colorless oil.

LCMS m/z 354.33; $^1$H NMR (400 MHz, DMSO-d$_6$) δ 8.24-8.17 (m, 1H), 7.98 (d, J=8.3 Hz, 1H), 7.75 (ddd, J=8.2, 4.6, 3.2 Hz, 1H), 4.44 (br. s., 2H), 3.88 (d, J=3.9 Hz, 2H), 3.69-3.45 (m, 21H).

EXAMPLE 7

Synthesis of [$^{18}$F]-3-(2-(2-(2-(2-azidoethoxy)ethoxy)ethoxy)ethoxy)-2-fluoropyridine using 3-(2-(2-(2-(2-azidoethoxy)ethoxy)ethoxy)ethoxy)-N,N,N-trimethylpyridin-2-aminium, trifluoromethanesulfonate salt

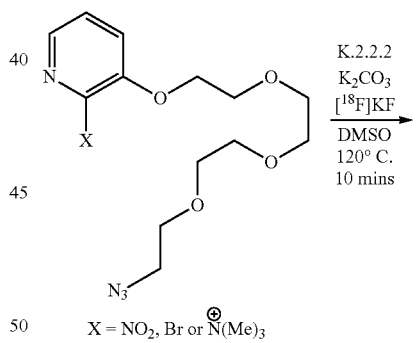

X = NO$_2$, Br or $\overset{\oplus}{N}$(Me)$_3$

An aqueous [$^{18}$F]-Fluoride solution (2.0 ml, 33.3 GBq/ 900 mCi) was purchased from P.E.T. Net® Pharmaceuticals in West Point PA and directly transferred to a Sep-Pak light QMA [The Sep-Pak light QMA cartridge was pre-conditioned sequentially with 5 ml of 0.5 M potassium bicarbonate, 5 ml of deionized water, and 5 ml of MeCN before use.] Upon completion of this transfer, the aqueous [$^{18}$F] fluoride was released from the QMA Sep-Pak by the sequential addition of potassium carbonate (15 mg/ml; 0.1 ml) followed by a mixture of potassium carbonate (30 mg/ml, 0.1 ml), 4,7,13,16,21,24-hexaoxa-1,10-diazabicyclo[8.8.8]hexacosane (15 mg, 0.04 mmol) and 1.2 ml of MeCN. The solvent was evaporated under a gentle stream of nitrogen at 90° C. and vacuum. Azeotropic drying was repeated twice with 1 ml portions of acetonitrile to generate the anhydrous K.2.2.2/K[$^{18}$F]F complex. 3-(2-(2-(2-(2-azidoethoxy)ethoxy)ethoxy)ethoxy)-N,N,N-trimethylpyridin-2-aminium, trifluoromethanesulfonate salt (2 mg, 5.6 μmol) was dissolved in 500 microliters of DMSO and added to the dried cryptand. This solution was heated at 120° C. for 10 minutes. After this time, the crude reaction mixture was diluted with 3 ml of DI water. The entire contents of the crude reaction mixture was then transferred, loaded, and purified using reverse phase HPLC under the following conditions: HPLC Column: Luna C18 250×10 Solvent A: 0.1% TFA in DI water; solvent B: 0.1% TFA in acetonitrile at a flow rate of 4.6 ml/minute using isocratic method 32% B while the UV was monitored at 280 nm. [$^{18}$F]-3-(2-(2-(2-(2-azidoethoxy)ethoxy)ethoxy)ethoxy)-2-fluoropyridine was isolated at the 24 min mark of the chromatogram and collect over a 2 minute period. This product was collected into a 100 ml flask that contained 10 ml of DI water and the entire contents were delivered to a Sep-Pak Vac tC18 6 cc 1 g sep pack from Waters. 6.1 GBq/164 mCi of [$^{18}$F]-3-(2-(2-(2-(2-azidoethoxy)ethoxy)ethoxy)ethoxy)-2-fluoropyridine was isolated from this reaction. This was released from the sep-pak using 3 ml of ethanol and this solution was reduced with 98° C. heat source, a gentle stream of nitrogen, and vacuum over a 15 minute period until only a film remained in the vial. The final product was reconstituted in 100% 1× PBS buffer and was stable in this media for over 1 hour at 37° C.

The [$^{18}$F]-3-(2-(2-(2-(2-azidoethoxy)ethoxy)ethoxy)ethoxy)-2-fluoropyridine may be used to generate $^{18}$F-labeled products (e.g., $^{18}$F-labeled anti-PD-L1 macrocyclic peptides, as described below) by taking advantage of "click" azide-alkyne reaction with the appropriate peptides containing an alkynes.

EXAMPLE 8

Production of $^{18}$F-Radiolabeled Macrocyclic Peptide using "Click Chemistry"

A. Fluorination of the 4-PEG-tosyl-azide Precursor to form [$^{18}$F]-3-(2-(2-(2-(2-azidoethoxy)ethoxy)ethoxy)ethoxy)-2-fluoropyridine An aqueous [$^{18}$F]-Fluoride solution (2.0 ml, 29.6 GBq/800 mCi) was purchased from IBA in Towada and shipped to the BMS Princeton N.J. site and this sample was transferred within our custom made remote controlled synthesis. This solution was delivered to a Sep-Pak light QMA [The Sep-Pak light QMA cartridge was pre-conditioned sequentially with 5 ml of 0.5 M potassium bicarbonate, 5 ml of deionized water, and 5 ml of MeCN before use.] Upon completion of this transfer, the aqueous [$^{18}$F] fluoride was released from the QMA Sep-Pak by the addition of a mixture of potassium carbonate (30 mg/ml in distilled water (DI), 0.1 ml), 4,7,13,16,21,24-hexaoxa-1,10-diazabicyclo[8.8.8]hexacosane (15 mg, 0.04 mmol) and 1.4 ml of acetonitrile. The solvent was evaporated under a gentle stream of nitrogen at 90° C. and vacuum. Azeotropic drying was repeated twice with 1 ml portions of acetonitrile to generate the anhydrous K.2.2.2/K[$^{18}$F]F complex. Upon completion of this process the cryptand was further dried under full vacuum for a 15 minute period. The entire process took 35 minutes to complete.

To this dried [$^{18}$F]/cryptand solid was added 0.5 ml of 2 mg of 3-(2-(2-(2-(2-azidoethoxy)ethoxy)ethoxy)ethoxy)-2-nitropyridine in DMSO and this mixture was heated at 120° C. for 10 minutes. After this time the crude reaction mixture was diluted with 3 ml of distilled water and the entire contents were then transferred and loaded onto the following HPLC column and conditions: HPLC Column: Luna C18 250×10 mm; Solvent A: 0.1% trifluoroacetic acid (TFA) in DI water; Solvent B: 0.1% TFA in acetonitrile; flow rate 4.6 ml/min; pressure 1820 PSI; isocratic method 32% B; UV-280 nm. The [$^{18}$F]-3-(2-(2-(2-(2-azidoethoxy)ethoxy)ethoxy)ethoxy)-2-fluoropyridine ([$^{18}$F]-FPPEGA) product was isolated at the 24 minute mark of the chromatogram and was collected over a 2 minute period. This product was collected into a 100 ml flask that contained 15 ml of DI water and the entire contents were delivered to a Sep PakVac tC18 6 cc 1 g sep pack (PN WAT036795). The [$^{18}$F]-FPPEGA was released from the Sep Pak using 2.5 ml of ethanol and this solution was reduced with 98° C. $N_2$ and vacuum over a 15 minute period until dryness. This compound was dissolved in 0.1 ml DI water. This product was analysed using a Varian HPLC HPLC Column Luna C18 (2) 4.6×150 mm Solvent A: 0.1% TFA in DI water; Solvent B: 0.1% TFA in acetonitrile; flow rate 1.0 ml/min; gradient method 0 min 90% A 10% B; 15 mins 30% A 70% B; 17 mins 30% A 70% B; 18 mins 90% A 10% B; 20 mins 90% A 10% B; UV-280 nm. 14.1 GBq (380 mCi) of [$^{18}$F]-FPPEGA was isolated. This product was carried forward to complete the "click" chemistry with alkyne containing PD-L1 binding macrocyclic peptide.

B. Coupling of [$^{18}$F]-FPPEGA to Macrocyclic Peptide

A schematic for synthesizing [$^{18}$F]-radiolabeled macrocyclic peptide is shown in Figure (a)

(S)-2-(2-((6S,9S,12S,18R,21S,24S,27S,30S,33S,36S,38aS,40R,44R,47S,49aS)-36-((1H-indol-3-yl)methyl)-6-(2-amino-2-oxoethyl)-33-(2-aminoethyl)-47-(aminomethyl)-24,27-dibutyl-30-((1-(carboxymethyl)-1H-indol-3-yl)methyl)-40-hydroxy-12-(4-hydroxybenzyl)-21,44-diisobutyl-9,10,25,28-tetramethyl-5,8,11,14,20,23,26,29,32,35,38,43,46,49-tetradecaoxohexatetracontahydro-1H,5H-dipyrrolo[2,1-g1:2',1'-x][1]thia[4,7,10,13,16,19,22,25,31,34,37,40,43]tridecaazacyclopentatetracontine-18-carboxamido)acetamido)pent-4-ynoic acid (0.75 mg, 0.378 □mol) was dissolved in 0.250 ml of DI water and 0.25 ml of tert-butyl alcohol. To this solution was added a 0.250 ml DI water solution containing 1 mg cupric sulfate and 1 mg of sodium ascorbate. Finally, the 0.1 ml solution of 14.1 GBq (380 mCi) of [$^{18}$F]-FPPEGA (prepared as described in section A) was added and the reaction was gently mixed at ambient temperature for 20 minutes. To the contents of this crude reaction mixture was added a 0.5 ml of acetonitrile followed by 1.5 ml of DI water and this mixture was purified using a reverse phase HPLC column. HPLC Column: Luna C18 250×10 mm; Solvent A: 0.1% trifluoroacetic acid (TFA) in DI water; Solvent B: 0.1% TFA in acetonitrile; flow rate 4.6 ml/min; pressure 1820 PSI; isocratic method 37% B; UV-220 nm. The product was isolated between the 27-31 minute mark of the chromatogram and was collected over a 4 minute period as shown in figure (b). 2.5 GBq (67 mCi) of [$^{18}$F]-(S)-2-(2-(((6S,9S,12S,18R,21S,24S,27S,30S,33S,36S,38aS,40R,44S,47S,49aS)-36-((1H-indol-3-yl)methyl)-6-(2-amino-2-oxoethyl)-33-(2-aminoethyl)-47-(aminomethyl)-24,27-dibutyl-30-((1-(carboxymethyl)-1H-indol-3-yl)methyl)-40-hydroxy-12-(4-hydroxybenzyl)-21,44-diisobutyl-9,10,25,28-tetramethyl-5,8,11,14,20,23,26,29,32,35,38,43,46,49-tetradecaoxohexatetracontahydro-1H,5H-dipyrrolo[2,1-g1:2',1'-x][1]thia[4,7,10,13,16,19,22,25,28,31,34,37,40,43]tetradecaazacyclopentatetracontine-18-carboxamido)acetamido)-3-(1-(2-(2-(2-(2-((2-fluoropyridin-3-yl)oxy)ethoxy)ethoxy)ethoxy)ethyl)-1H-1,2,3-triazol-4-yl)propanoic acid was isolated. This solution was further diluted with 20 ml of DI water and this solution was transferred to a C-18 sep-pak (Waters 50 mg, that was pre-activated with 5 ml of ethanol, followed by 10 ml of DI water) to remove any organic solvent from the solution. This sep-pak was further washed with 10 ml of sterile water for injection. This product was released from the sep-pak with 0.5 ml of ethanol, sterile filtered into a sterile vial and diluted to a 5% ethanol by volume solution with saline for injection. This product was analyzed via reverse phase HPLC for as shown in figure (b): chemical identify with co-injection of non-radioactive standard, radiochemical purity and chemical purity, specific activity. The isolated product co-eluted with non-radioactive reference standard, was 100% radiochemically and 95% chemically pure, with a specific activity of 0.37 (10 mCi) GBq/nmol.

Analytical reverse phase HPLC was performed with the following parameters:

Zorbax SB-C18 250×4.6 mm column; Solvent A: 0.05% formic acid in DI water;

Solvent B: 0.05% in acetonitrile; flow rate 1.0 ml/min; gradient method 30% to 50% B over 20 minutes; UV-220 nm.

Figure (a)

A schematic for synthesizing [$^{18}$F] radiolabeled PD-L1 binding macrocyclic peptide

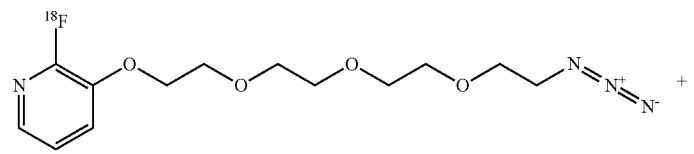

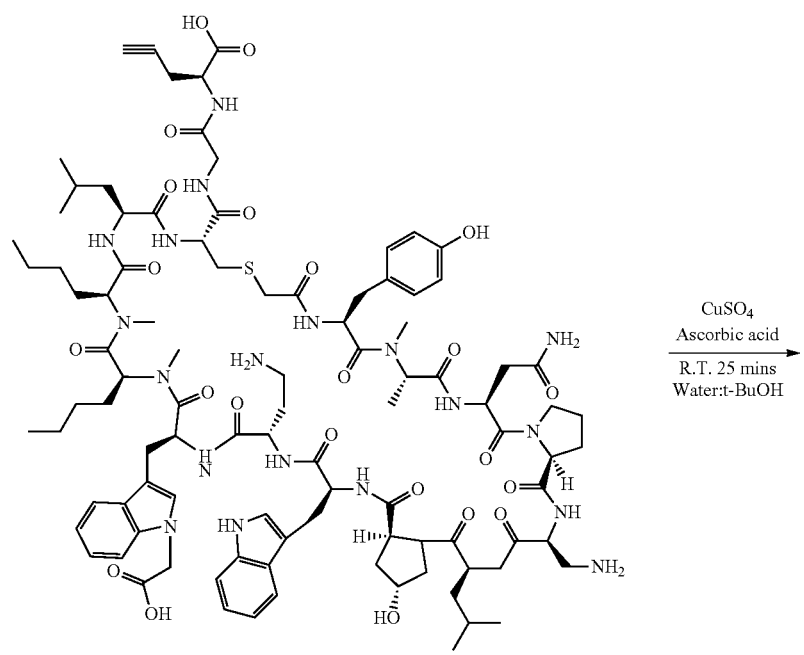

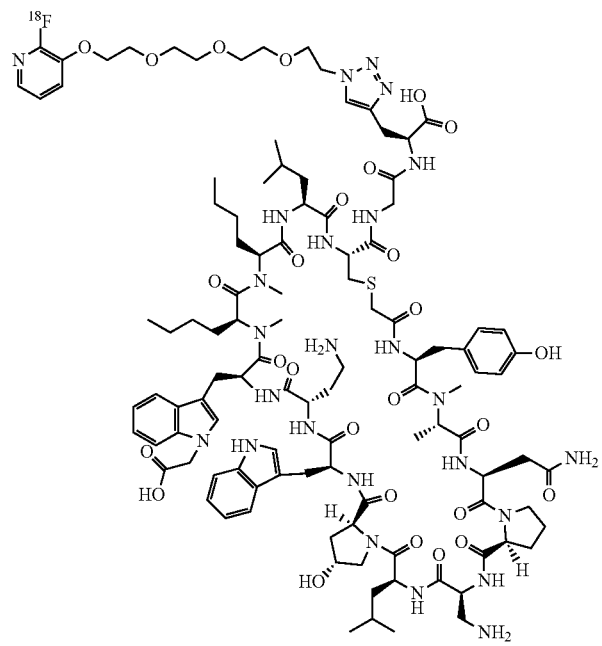

The of [¹⁸F]-(S)-2-(2-((6S,9S,12S,18R,21S,24S,27S,30S,33S,36S,38aS,40R,44S,47S,49aS)-36-((1H-indol-3-yl)methyl)-6-(2-amino-2-oxoethyl)-33-(2-aminoethyl)-47-(aminomethyl)-24,27-dibutyl-30-((1-(carboxymethyl)-1H-indol-3-yl)methyl)-40-hydroxy-12-(4-hydroxybenzyl)-21,44-diisobutyl-9,10,25,28-tetramethyl-5,8,11,14,20,23,26,29,32,35,38,43,46,49-tetradecaoxohexatetracontahydro-1H,5H-dipyrrolo[2,1-g1:2',1'-x][1]thia[4,7,10,13,16,19,22,25,28,31,34,37,40,43]tetradecaazacyclopentatetracontine-18-carboxamido)acetamido)-3-(1-(2-(2-(2-(2-((2-fluoropyridin-3-yl)oxy)ethoxy)ethoxy)ethoxy)ethyl)-1H-1,2,3-triazol-4-yl)propanoic acid can be used in a variety of in vitro and/or in vivo imaging applications, including diagnostic imaging, basic research, and radiotherapeutic applications. Specific examples of possible diagnostic imaging and radiotherapeutic applications, include determining the location, the relative activity and/or quantifying of PD-L1 positive tumors, radioimmunoassay of PD-L1 positive tumors, and autoradiography to determine the distribution of PD-L1 positive tumors in a mammal or an organ or tissue sample thereof.

In particular, the [¹⁸F]-(S)-2-(2-((6S,9S,12S,18R,21S,24S,27S,30S,33S,36S,38aS,40R,44S,47S,49aS)-36-((1H-indol-3-yl)methyl)-6-(2-amino-2-oxoethyl)-33-(2-aminoethyl)-47-(aminomethyl)-24,27-dibutyl-30-((1-(carboxymethyl)-1H-indol-3-yl)methyl)-40-hydroxy-12-(4-hydroxybenzyl)-21,44-diisobutyl-9,10,25,28-tetramethyl-5,8,11,14,20,23,26,29,32,35,38,43,46,49-tetradecaoxohexatetracontahydro-1H,5H-dipyrrolo[2,1-g1:2',1'-x][1]thia[4,7,10,13,16,19,22,25,28,31,34,37,40,43]tetradecaazacyclopentatetracontine-18-carboxamido)acetamido)-3-(1-(2-(2-(2-(2-((2-fluoropyridin-3-yl)oxy)ethoxy)ethoxy)ethoxy)ethyl)-1H-1,2,3-triazol-4-yl)propanoic acid is useful for positron emission tomographic (PET) imaging of PD-L1 positive tumors in the lung, heart, kidneys, liver and skin and other organs of humans and experimental animals. PET imaging using the [¹⁸F]-(S)-2-(2-((6S,9S,12S,18R,21S,24S,27S,30S,33S,36S,38aS,40R,44S,47S,49aS)-36-((1H-indol-3-yl)methyl)-6-(2-amino-2-oxoethyl)-33-(2-aminoethyl)-47-(aminomethyl)-24,27-dibutyl-30-((1-(carboxymethyl)-1H-indol-3-yl)methyl)-40-hydroxy-12-(4-hydroxybenzyl)-21,44-diisobutyl-9,10,25,28-tetramethyl-5,8,11,14,20,23,26,29,32,35,38,43,46,49-tetradecaoxohexatetracontahydro-1H,5H-dipyrrolo[2,1-g1:2',1'-x][1]thia[4,7,10,13,16,19,22,25,28,31,34,37,40,43]tetradecaazacyclopentatetracontine-18-carboxamido)acetamido)-3-(1-(2-(2-(2-(2-((2-fluoropyridin-3-yl)oxy)ethoxy)ethoxy)ethoxy)ethyl)-1H-1,2,3-triazol-4-yl)propanoic acid can be used to obtain the following information: relationship between level of tissue occupancy by candidate PD-L1 tumor-treating medicaments and clinical efficacy in patients; dose selection for clinical trials of PD-L1 tumor-treating medicaments prior to initiation of long term clinical studies; comparative potencies of structurally novel PD-L1 tumor-treating medicaments; investigating the influence of PD-L1 tumor-treating medicaments on in vivo transporter affinity and density during the treatment of clinical targets with PD-L1 tumor-treating medicaments; changes in the density and distribution of PD-L1 positive tumors during effective and ineffective treatment.

EXAMPLE 9

Automated Preparation of [$^{18}$F]-3-(2-(2-(2-(2-azido-ethoxy)ethoxy)ethoxy)ethoxy)-2-fluoropyridine According to the General Procedure for the Synthesis Radiosynthesis on GE TRACERlab FX2 N Synthesis Unit

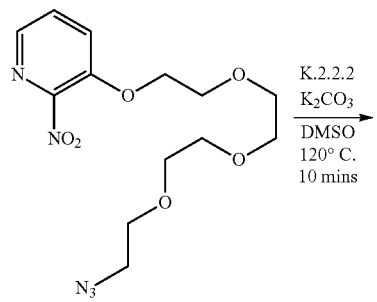

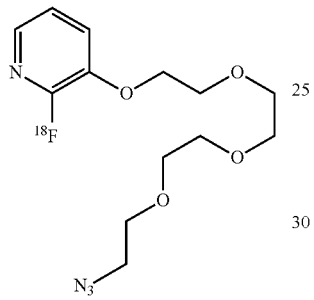

Automated Synthesis using commercial TRACERlab FX2 N Synthesis module (GE)

The automated synthesis of [$^{18}$F]-3-(2-(2-(2-(2-azidoethoxy)ethoxy)ethoxy)ethoxy)-2-fluoropyridine was carried out using a non-cassette type GE TRACERlab FX2 N Synthesis module. The setup of the synthesis unit is summarized in Table ( ). The aqueous [$^{18}$F]-Fluoride solution (2.0 ml, 29.6 GBq/800 mCi) was delivered to a Sep-Pak light QMA [The Sep-Pak light QMA cartridge was pre-conditioned sequentially with 5 ml of 0.5 M potassium bicarbonate, 5 ml of deionized water, and 5 ml of acetonitrile before use.] Upon completion of this transfer, the aqueous [$^{18}$F] fluoride was released from the QMA Sep-Pak by the addition of a the elution mixture (from "V1") into the reactor. The solvent was evaporated under a gentle stream of nitrogen and vacuum. The solution of precursor (from "V3") was added to the dried cryptand residue and this reaction mixture was heated 120° C. for 10 minutes. Then 4 ml of distilled water (from "V4") was added to the crude reaction mixture in the reactor and the mixture is transferred to the 5 ml sample injection loop of the semi-preparative HPLC via a liquid sensor which controls the end of the loading. The mixture is loaded onto the semi-preparative HPLC column (Luna C18(2). 250×10 mm, Phenomenex). A mixture of 35% acetonitrile in an aqueous 0.1% trifluoroacetic acid solution was flushed through the column at a rate of 4.6 ml per minute. The product was collected from this HPLC column into the dilution flask which contained 15 ml distilled water and its entire contents were transferred to a tC18 1 gram, solid phase extraction cartridge. 352 mCi (13 GBq) of [$^{18}$F]-3-(2-(2-(2-(2-azidoethoxy)ethoxy)ethoxy)ethoxy)- 2-fluoropyridine was released from this cartridge (from "V14") with 3 ml of ethanol and may be used to generate $^{18}$F labeled peptide products by taking advantage of "click" azide-alkyne reaction with the appropriate peptide containing an alkynes.

TABLE (1)

| Vial 1 (V1) | 16 mg K.2.2.2, 3 mg Potassium carbonate, dissolved in 0.1 ml of distilled water and 1.4 ml of acetonitrile |
|---|---|
| Vial 3 (V3) | 2 mg 3-(2-(2-(2-(2-azidoethoxy)ethoxy)ethoxy)ethoxy)-2-nitropyridine in 0.5 ml DMSO |
| Vial 4 (V4) | 4 ml of distilled water |
| Vial 14 (V14) | 3 ml of 100% ethanol |
| Dilution Flask | 15 ml of distilled water |
| Cartridge 1 (C1) | tC18 6 cc 1 g sep pack |
| HPLC Column | Luna C18(2), 250 × 10 mm, 5 □m, Phenomenex |
| HPLC Solvent | 35% acetonitrile in an aqueous 0.1% trifluoroacetitic acid solution |
| HPLC flow | 4.6 ml/min |

Example 10

Automated Preparation of [$^{18}$F]-3-(2-(2-(2-(2-azido-ethoxy)ethoxy)ethoxy)ethoxy)-2-fluoropyridine According to the General Procedure for the Synthesis Radiosynthesis on IBA Synthera Synthesis Unit

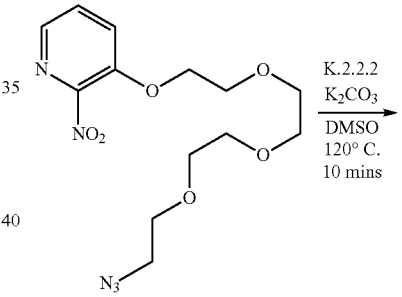

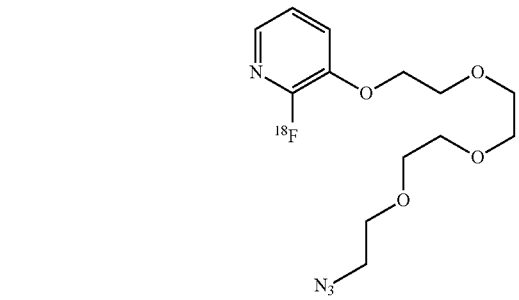

Automated Synthesis using Commercial Synthera Synthesis Module (IBA)

The automated synthesis of [$^{18}$F]-3-(2-(2-(2-(2-azidoethoxy)ethoxy)ethoxy)ethoxy)-2-fluoropyridine was carried out using a cassette type IBA Synthera Synthesis module and an appropriately assembled integrator fluidic processor kit. The integrator fluidic processor (IFP) kit was loaded with appropriate precursors for this synthesis and is summarized in Table ( ). The purification was performed on an Varian HPLC unit. The filling of the injection loop of the HPLC was controlled by a steady stream of nitrogen on the HPLC unit. The setup of both automates are summarized in Table ( ). The aqueous [$^{18}$F]-Fluoride solution (2.0 ml, 29.6 GBq/800 mCi) was delivered to a Sep-Pak light QMA [The Sep-Pak light QMA cartridge was pre-conditioned sequentially with 5 ml of 0.5 M potassium bicarbonate, 5 ml of deionized water, and 5 ml of acetonitrile before use.]. Upon completion of this transfer, the aqueous [$^{18}$F] fluoride was released from the QMA Sep-Pak by the addition of a the elution mixture (from "V1") into the reactor. The solvent was evaporated under a gentle stream of nitrogen and vacuum. The solution of precursor (from "V2") was added to the dried cryptand residue and this reaction mixture was heated 120° C. for 10 minutes. Then 3 ml of distilled water (from "V4") was added to the crude reaction mixture in the reactor and the mixture is transferred to the 5 ml sample injection loop of the semi-preparative HPLC via a liquid sensor which controls the end of the loading. The mixture is loaded onto the semi-preparative HPLC column (Luna C18 (2). 250×10 mm, Phenomenex). A mixture of 35% acetonitrile in an aqueous 0.1% trifluoroacetic acid solution was flushed through the column at a rate of 4.6 ml per minute. The product was collected from this HPLC column into the dilution flask which contained 15 ml distilled water and its entire contents were transferred to a tC18 1 gram, solid phase extraction cartridge. 325 mCi (12 GBq) of [$^{18}$F]-3-(2-(2-(2-(2-azidoethoxy)ethoxy)ethoxy)ethoxy)-2-fluoropyridine was released from this cartridge with 3 ml of ethanol and may be used to generate $^{18}$F labeled peptide products by taking advantage of "click" azide-alkyne reaction with the appropriate peptide containing an alkynes.

TABLE (2)

| | |
|---|---|
| Vial 1 (V1) | 22 mg K.2.2.2, 4 mg Potassium carbonate, dissolved in 0.3 ml of distilled water and 0.3 ml of acetonitrile |
| Vial 2 (V2) | 2 mg 3-(2-(2-(2-(2-azidoethoxy)ethoxy)ethoxy)ethoxy)-2-nitropyridine in 0.5 ml DMSO |
| Vial 4 (V4) | 3 ml of distilled water |
| Dilution Flask | 15 ml of distilled water |
| Cartridge 1 (C1) | tC18 6 cc 1 g sep pack |
| HPLC Column | Luna C18(2), 250 × 10 mm, 5 □m, Phenomenex |
| HPLC Solvent | 35% acetonitrile in an aqueous 0.1% trifluoroacetitic acid solution |
| HPLC flow | 4.6 ml/min |

EXAMPLE 11

Distinguishing PD-L1-Positive Tumors from PD-L1-Negative Tumors with an Anti-PD-L1 Macrocyclic Peptide Imaging Agent For PET imaging, rapid blood clearance rates provide an advantage over more slowly clearing agents, such as antibodies, by minimizing the amount of time needed for "background" probe signals to deplete from non-relevant tissue. In the clinic, long blood half-life antibody-based-PET tracers may require several days of waiting post injection before images can be collected. Rapid clearing probes open the door to high contrast images that can be collected on the same day the probe is injected, and very importantly, they can also serve to reduce overall radiation exposure to the animals studied or patients examined.

In this experiment, the [$^{18}$F]labelled macrocyclic PD-L1 peptide was produced as described in the above Examples, was tested for its ability to discriminate between hPD-L1-positive tumors and hPD-L1-negative tumors in mice.

Figure 2:
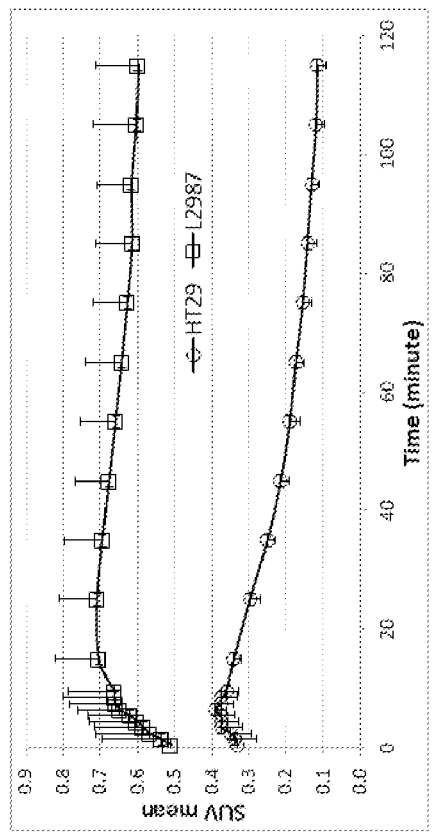
FIGS. 2A and 2B shows averaged time-activity curves for saline and labelled macrocyclic PD-L1 peptide radiotracers.
Figure 2:
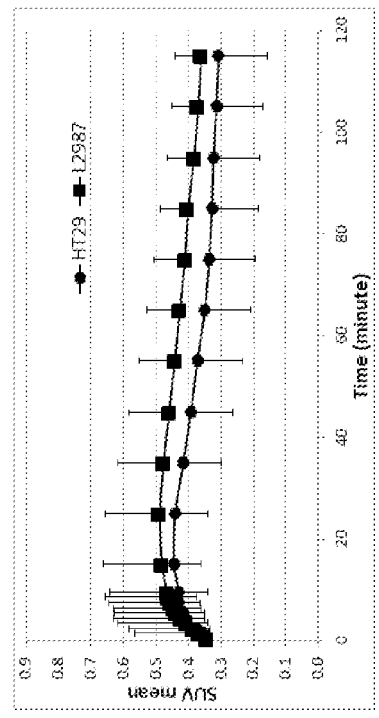

Mice bearing bilateral xenograft tumors were produced by introducing 2×10$^6$ hPD-L1(+) L2987 human lung carcinoma cells and 4×10$^6$ hPD-L1(−) HT-29 human colon carcinoma cells subcutaneously on opposite sides of the mouse. Once tumors reached approximately 300 mm$^3$ (approximately 2-3 weeks after cell implantation), animals were selected for imaging. The body weight and tumor size of each study were measured and recorded on the imaging day before imaging procedure. Mice were placed in an anesthetic induction chamber and 3% isoflurane inhalant anesthesia was delivered in 100% O$_2$ at a rate of 1-1.5 L/min. Once sedated, mice were removed from the induction chamber and placed into a plexiglass 4-chamber mouse hotel (custom-made by BMS-Applied Biotechnology group), while continuing to receive 1-1.5% isoflurane inhalant anesthesia and delivered in 100% O$_2$ at a rate of 2 L/min via the nose-cone. Animal were kept warm using an external standalone temperature regulating unit (M2M Imaging Corp) to prevent hypothermia during imaging. Mouse respiration was continuously monitored during imaging procedures and isoflurane may be adjusted dependent on depth of anesthesia. Mice were then placed into a custom animal holder with capacity for 4 animals, where they remained under anesthesia for the duration of the study. The animal holder was transferred to the microPET® F120™ scanner (Siemens Preclinical Solutions, Knoxville, Tenn.). The axial field of view of this instrument is 7.6 cm. With this limitation, animals were positioned such that the scanning region was from immediately in front of the eyes to approximately the base of the tail. A 10-minute transmission image was first acquired using a $^{57}$Co point source for the purpose of attenuation correction of the final PET images. Following the transmission scan, radiotracer solutions were administered via the previously installed tail vein catheters and a 2 hour emission image was acquired. Injected radiotracer solutions were injected into a total 8 mice (body weight: 22.2±2.0 gram) with tumor volumes 203.0±51.4 mm$^3$ for HT-29 and 422.9±128.4 mm$^3$ for L2987 were imaged 16-17 days post cell implantation. Each mouse received a single injection of SC dose of PD-L1 binding macrocyclic peptide 60 mg/kg (N=4) or saline (N=4) 30 minute before the [$^{18}$F]labelled macrocyclic PD-L1 peptide (124.0±8.4 μCi, tracer mass: 1.0±0.4 μg/kg) IV injection. Images were reconstructed using a maxiumum a posteriori (MAP) algorithm with attenuation correction using the collected transmission images and corrected for radioisotope decay. In the final images, regions of interest (ROIs) were drawn around the tumor boundary using ASIPro software (Siemens Preclinical Solutions). Time-activity curves were calculated for each ROI to yield a quantitative view of radiotracer within the tumor volume over the course of the 2 hour emission image. For final comparison, individual time-activity curves were normalized based on the injected radiotracer dose for each specific animal. Radiotracer uptake was compared across tumors using the final 10 minutes of each time-activity curve (90-100 minutes post-radiotracer injection). Using this methodology, radiotracer uptake in hPD-L1(+) L2987 xenografts was 8.1× that seen hPD-L1(−) HT-29 xenografts in animals receiving only the [$^{18}$F]labelled macrocyclic PD-L1 peptide radiotracer. In animals receiving SC dose of PD-L1 binding macrocyclic peptide 60 mg/kg 30 minutes before the radiotracer injection. Uptake in the hPD-L1(+) L2987 xenografts was only 0.7×that seen in hPD-L1(−) HT-29 xenografts (FIG. 1, FIG. 2 and Table 3).

TABLE 3

The standard uptake values (SUV) in HT-29 and L2987 tumors derived from PET images in Example 11

| PD-L1 binding macrocyclic peptide | Mouse # | Body weight (gram) | Volume of HT-29 (mm³) | Volume of L2987 (mm³) | Injected dose (µCi) | Tracer mass (µg/kg) | SUV in HT29 | SUV in L2987 |
|---|---|---|---|---|---|---|---|---|
| 0 mg/kg (Saline) | Mouse 3 | 20.4 | 180 | 500 | 132.6 | 4.60 | 0.036 | 0.213 |
| | Mouse 7 | 21.3 | 144 | 320 | 110.9 | 4.63 | 0.033 | 0.231 |
| | Mouse 19 | 24.4 | 162 | 245 | 100.5 | 1.45 | 0.047 | 0.452 |
| | Mouse 23 | 22.1 | 87.5 | 126 | 81.7 | 1.66 | 0.031 | 0.297 |
| | Mean | 22.1 | 143.4 | 297.8 | 106.4 | 3.1 | 0.037 | 0.298 |
| | (Stdev) | (1.7) | (40.0) | (156.7) | (21.2) | (1.8) | (0.007) | (0.109) |
| 60 mg/kg | Mouse 6 | 23.0 | 64 | 171.5 | 114.4 | 4.36 | 0.102 | 0.060 |
| | Mouse 12 | 22.0 | 126 | 288 | 90.5 | 4.58 | 0.084 | 0.055 |
| | Mouse 22 | 23 | 126 | 760.5 | 71.3 | 1.41 | 0.030 | 0.042 |
| | Mouse 28 | 23.8 | 108 | 320 | 118.1 | 2.63 | 0.065 | 0.043 |
| | Mean | 23.0 | 106.0 | 385.0 | 98.6 | 3.2 | 0.071 | 0.050 |
| | (Stdev) | (0.7) | (29.3) | (258.3) | (21.9) | (1.5) | (0.031) | (0.009) |

These results provide direct visualization of differentiation of hPD-L1(+) vs. hPD-L1(−) xenograft tumors in vivo. Specificity was further demonstrated by predosing PD-L1 binding macrocyclic peptide 60 mg/kg 30 minutes before the radiotracer injection, resulting in a reduction of radiotracer uptake in hPD-L1(+) tumors to the level of hPD-L1(−) xenografts. This further validates the use of PD-L1 macrocyclic peptides for visualization of PD-L1 tissue expression using PET imaging.

EXAMPLE 12

PET Imaging in Non-Human Primate with an Anti-PD-L1 Macrocyclic Peptide Imaging Agent The anti-PD-L1 millamolecule-based imaging agents also showed similar results when performed in cynomolgus monkeys. In these studies, the [$^{18}$F]labelled macrocyclic PD-L1 peptide, produced as described in the above Examples, was tested for its ability to produce high-contrast images in cynomolgus monkeys. The anti-PD-L1 macrocyclic peptides described here maintain high affinity for cynomolgus PD-L1 (but have low affinity for rodent PD-L1). Furthermore, as cynomolgus monkeys do not contain PD-L1 (+) tumors as in mouse models, imaging performance was assessed primarily on the background levels measured in the images in the context of endogenous PD-L1 expression (with low background enabling the potential for high-sensitivity detection of PD-L1(+) tissues). In these studies, background levels in the resulting PET images were very low, with notable radiotracer accumulation noted mainly in the kidneys, spleen, and bladder.

Cynomolgus male monkeys with a previously installed vascular access port (VAP) were anesthetized with 0.02 mg/kg atropine, 5 mg/kg Telazol and 0.01 mg/kg buprenorphine I.M. (all drawn into a single syringe). An i.v. catheter is then placed in the cephalic vessel for fluid administration during the imaging procedure to maintain hydration. Animals were intubated with an endotracheal tube—usually 3.0 mm and transferred to the imaging bed of a microPET® F220TM PET instrument (Siemens Preclinical Solutions, Knoxville, Tenn.). Anesthesia was maintained with isoflurane and oxygen and I.V. fluids (LRS) were administered at a rate of 6 ml/kg/hr during the imaging procedure. As the axial field of view of the microPET® F220™ instrument is only 7.6 cm, images over 5 distinct bed positions were acquired to create a composite image of the animals from just above the heart through approximately the pelvis.

For each field of view, a 10 minute transmission image was first acquired using a $^{57}$Co point source for the purpose of attenuation correction of the final PET images. Once transmission images were acquired for all bed positions, approximately 1.7 mCi (approximately 0.12 µg/kg) of the [$^{18}$F]labelled macrocyclic PD-L1 peptide radiotracer was administered via the installed VAP. 5 minute duration emission scans were then sequentially acquired for each bed position, beginning at position 1 centered approximately at the heart and moving toward the pelvis of the animal. Once images were acquired at each position (1 through 5), the imaging bed was moved back to bed position 1 and the process was repeated. Using this procedure, a total of 5 distinct images were acquired for each bed position over the duration of the imaging study.

Figure 3:
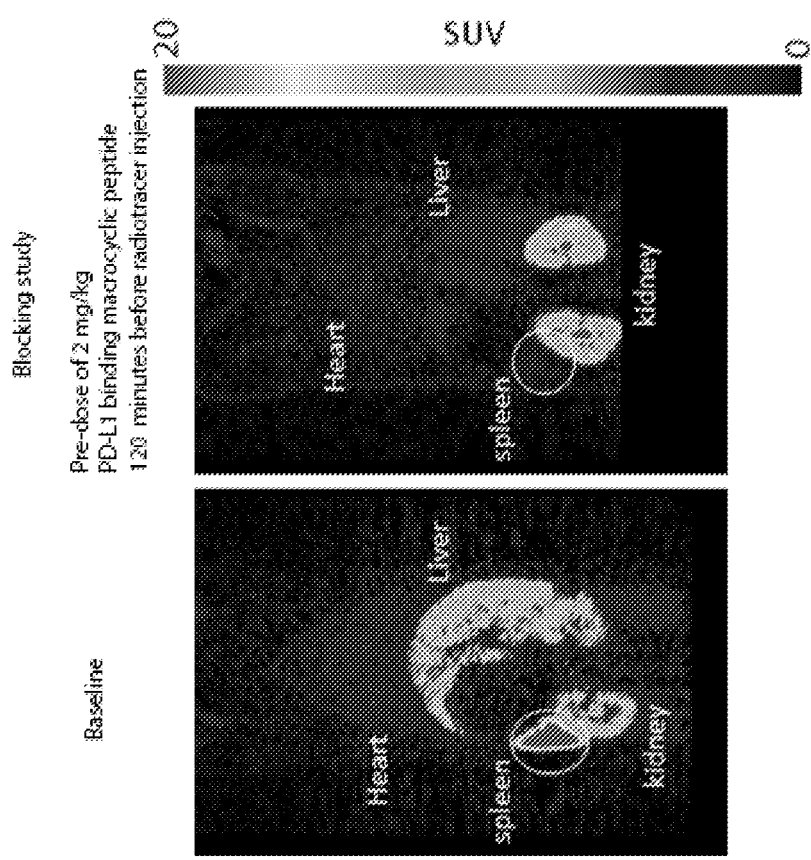
FIG. 3 is a representative PET images of labelled macrocyclic PD-L1 peptide radiotracer in non-human primate.

Individual images were reconstructed using a filtered back projection (FBP) algorithm with attenuation correction using the collected transmission images and corrected for radioisotope decay. Final composite images were then produced by aligning images from all 5 bed positions obtained from a single pass (i.e. a single composite image was produced from each set of sequential images from bed positions 1 through 5) covering the duration of the imaging study. Final images were visually inspected to note areas of visible radiotracer uptake (i.e. spleen, liver, kidney) and background tissue (muscle) (FIG. 3). Background accumulation of the [$^{18}$F]labelled macrocyclic PD-L1 peptide radiotracer was very low, with little signal visible in background tissues such as muscle. Additionally, uptake was verified in the spleen, which is PD-L1(+) based on immunohistochemistry and mRNA expression. Thus, studies in cynomolgus monkeys demonstrate the potential for high-sensitivity PD-L1 imaging in the context of endogenous PD-L1. To determine the nature of the specific binding in the cynomolgus monkey spleen a blocking study was conducted in the following manner.

The cynomolgus monkey (4.4 kg, male) received a single IV injection of [$^{18}$F]labelled macrocyclic PD-L1 peptide radiotracer (~1.7 mCi, mass: 0.21 µg/kg) at baseline. On the following day (post-dose), the same NHP received a single SC dose of 2 mg/kg anti-PD-L1 binding macrocyclic peptide at 2 hours before radiotracer injection (~1.7 mCi, mass: 0.12 µg/kg). The tracer uptake in various organs are listed in Table 4. Representative PET images of baseline and post-dose are plotted in FIG. 3. The plasma concentrations of the anti-PD-L1 binding macrocyclic peptide were measured at 0, 10, 30, 60, 90 minutes after radiotracer injection on each imaging day (Table 4). A specific binding signal was observed within the spleen of the non-human primate with 93% of tracer uptake was blocked with 2 mg/kg of a specific PD-L1 binding macrocyclic peptide.

PET studies in rodent and cynomolgus monkey show that $^{18}$F labeled anti-human PD-L1 macrocyclic peptide provide strong and specific probes for in vivo labeling of PD-L1 positive tissues with the potential for high-sensitivity detection of tissues with low level PD-L1 expression.

In vivo imaging experiments were also conducted with an anti-PD-L1 antibody, and the areas that this imaging agent detected were the same areas that were detected with the PD-L1 imaging agent, therefore confirming that anti-PD-L1 millamolecule imaging agents successfully detect PD-L1 positive cells in vivo.

TABLE 4

Tracer SUV in each organ in baseline and post-dose with 2 mg/kg PD-L1 binding macrocyclic peptide.

| SUV | Baseline | Blocked with 2 mg/kg of PD-L1 binding macrocyclic peptide | % Change |
|---|---|---|---|
| Spleen | 19.720 | 1.423 | −92.8% |
| Kidney Pelvis | 8.855 | 24.061 | 171.7% |
| Kidney Cortex | 8.420 | 10.846 | 28.8% |
| Duodenum | 8.840 | 8.756 | −0.9% |
| Liver | 9.163 | 3.165 | −65.5% |
| Gallbladder | 2.776 | 1.128 | −59.4% |
| Lung | 1.856 | 0.793 | −57.3% |
| Muscle | 0.521 | 0.341 | −34.7% |
| Thymus | 1.992 | 0.931 | −53.3% |

* % change = (SUV in before − SUV in after)/SUV in before

EXAMPLE 13

Figure 4:
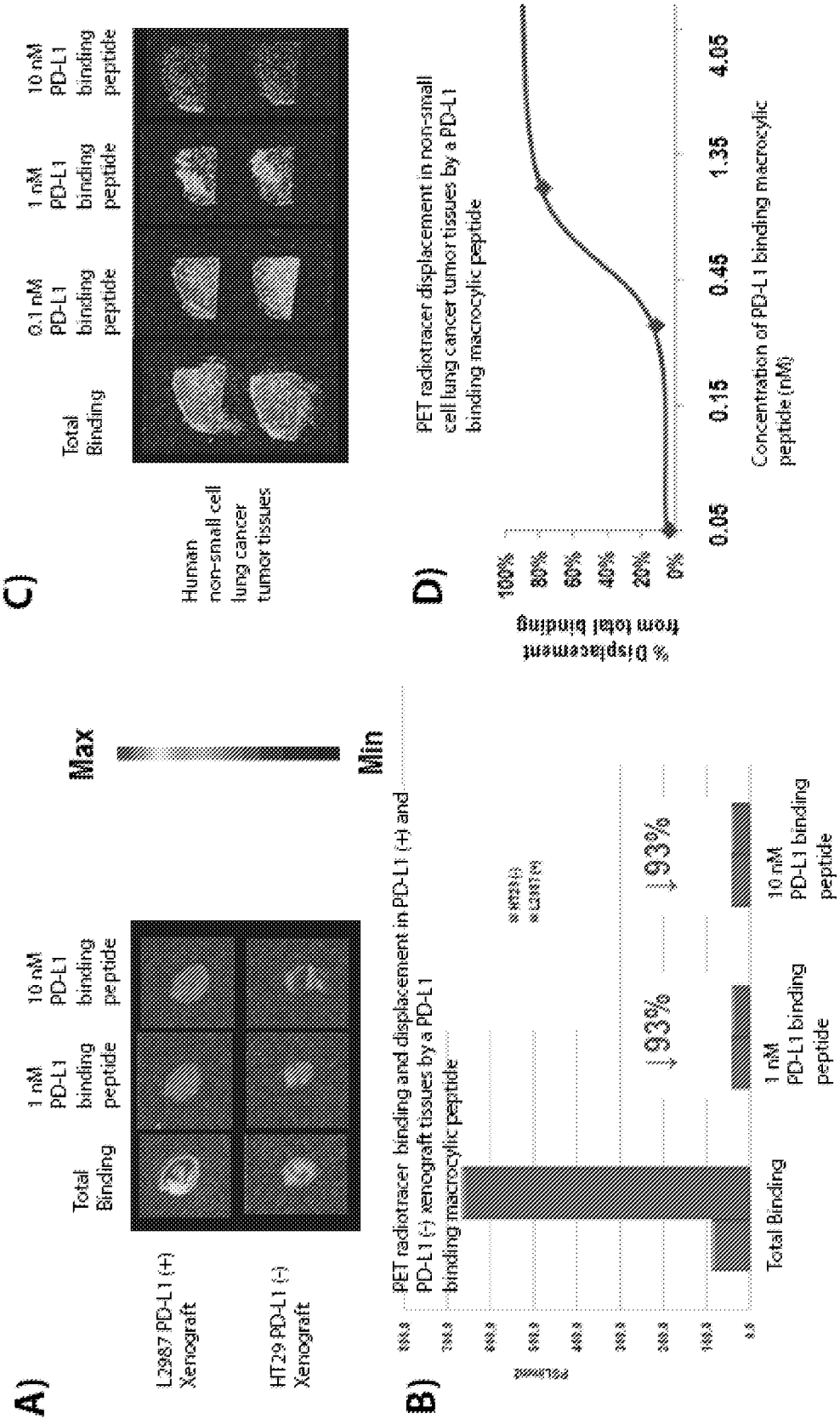
FIG. 4 shows autoradiogram images of labelled macrocyclic PD-L1 peptide radiotracer in xenograft (A&B) and human non-small cell lung cancer biopsied tissues (C&D).

In Vitro Autoradiography with [$^{18}$F]Labelled Macrocyclic PD-L1 Peptide Radiotracer Human lung tumor tissues were embedded in OCT and chilled in 2-methylbutane for 2-5 minutes until frozen. Samples were stored in −80° C. degree freezer until use. Human xenograft tissues were also included in the assay. Mice bearing bilateral xenografts were produced by introducing 2×10$^6$hPD-L1(+) L2987 human lung carcinoma cells and 4×10$^6$hPD-L1(−) HT-29 human colon carcinoma cells subcutaneously on opposite sides of the mouse. Once resulting xenograft tumors reached appropriate size (approx. 200-300 mm$^3$), mice were anesthetized with 2% isoflurane and sacrificed via cervical dislocation. Fresh tumor tissues were excised, immersed into OCT and chilled in 2-methylbutane for 2-5 minutes until frozen. The tissues were then wrapped in foil/ZIPLOC® bag and stored at −80° C. until use. For all tissues (human lung tumor and xenografts) sections of 5 µm thickness (collected as 2 sections/slide) were cut using a cryostat, thaw-mounted on glass microscope slides, and allowed to air dry for approximately 30 minutes. Blocking studies with cold (unlabelled) peptide at 0.1 nM, 1 nM, and 10 nM respectively. The individual slides, 1 slide per concentration, were transferred to glass slide incubation chambers for incubation. Separately, a stock solution of 0.25 nM [$^{18}$F]-(S)-2-(2-((6S,9S,12S,18R,21S,24S,27S,30S,33S,36S,38aS,40R,44S,47S,49aS)-36-((1H-indol-3-yl)methyl)-6-(2-amino-2-oxoethyl)-33-(2-amino-ethyl)-47-(aminomethyl)-24,27-dibutyl-30-((1-(carboxymethyl)-1H-indol-3-yl)methyl)-40-hydroxy-12-(4-hydroxybenzyl)-21,44-diisobutyl-9,10,25,28-tetramethyl-5,8,11,14,20,23,26,29,32,35,38,43,46,49-tetradecaoxohexatetracontahydro-1H,5H-dipyrrolo[2,1-g1:2',1'-x][1]thia[4,7,10,13,16,19,22,25,28,31,34,37,40,43]tetradecaazacyclopentatetracontine-18-carboxamido)acetamido)-3-(1-(2-(2-(2-(2-((2-fluoropyridin-3-yl)oxy)ethoxy)ethoxy)ethyl)-1H-1,2,3-triazol-4-yl)propanoic acid was produced by diluting 10.6 µl of the original stock radioligand solution (7064 nM at the time of experiment) with 300 ml of tween 80. From this stock solution, 40 ml was added to each incubation chamber. One of these chambers contained only the radioligand buffer solution, which is referred to as the total binding section. Other incubation chambers received 40 ml of this stock solution along with the relevant concentration of blocking compound (unlabelled peptide at 0.1 nM, 1 nM, or 10 nM). Slides were incubated in the individual buffer solutions for 1 hour at room temperature to reach maximum binding. After incubation, slides from each treatment group were removed from the incubation solutions and placed in an ice-cold wash buffer (Tween 80) for 3 minutes and rinsed 4 separate times. Slides were then dried under a stream of cold air for approximately 30 minutes. The air-dried slides were exposed by placing the slides onto an imaging plate (BAS-SR 3545S) overnight at room temperature. The imaging plate was scanned using the bioimaging analyzer (Fujifilm Fluorescent Image Analyzer, FLA-9000). The pixel size of the autoradiogram images was 100 µm. Image analysis was performed using the Multi-Gauge software. The regions of interest (ROIs) were drawn to surround the entire tumor tissue in all study groups. Autoradiography signals from tissue-associated radioactivity were quantified from these ROIs. The apparent displacement of the [$^{18}$F]labelled macrocyclic PD-L1 peptide radiotracer when compared to the total binding sections was determined for 3 different concentrations (0.1 nM, 1 nM, and 10 nM) of unlabeled peptide in both human lung tumor sections as well as human xenograft sections. A dose dependent displacement of [$^{18}$F] labelled macrocyclic PD-L1 peptide radiotracer was seen in all tissue sections with the addition of unlabelled peptide (FIG. 4). Serial 5 µm tissue sections from each tissue were subjected to an anti-human-PD-L1 immunohistochemical procedure to verify the level of PD-L1 antigen expression in the samples confirmed PD-L1 expression in human lung samples.

Those skilled in the art will recognize, or be able to ascertain using no more than routine experimentation, many equivalents of the specific embodiments described herein. Such equivalents are intended to be encompassed by the following claims.
What is claimed is:
1. A compound of formula (I)
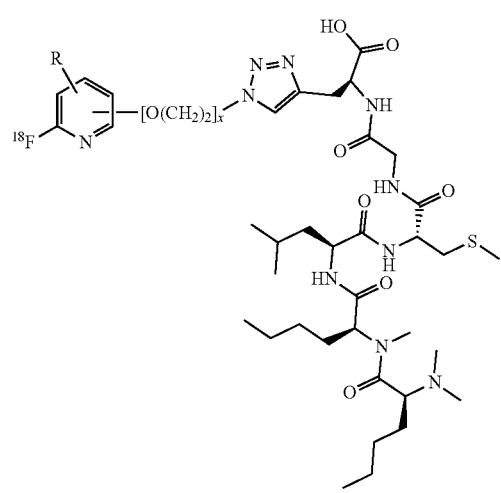
(I)
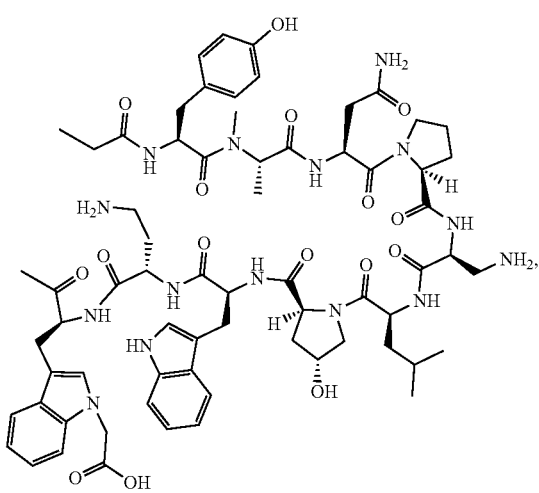
or a pharmaceutically acceptable salt thereof, wherein x is an integer from 1 to 8 and R is a $C_1$-$C_6$alkyl group.
2. A compound of claim 1 of formula (II)
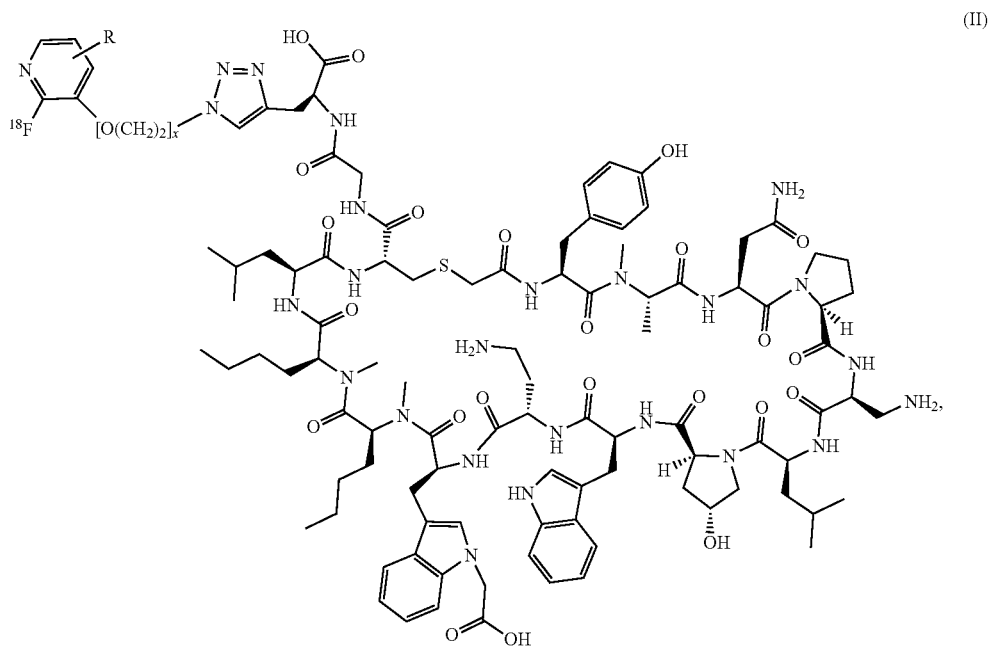
(II)

or a pharmaceutically acceptable salt thereof, wherein x is an integer from 1 to 8 and R is hydrogen or a $C_1$-$C_6$alkyl group.

3. A compound of claim 1 of formula (III)

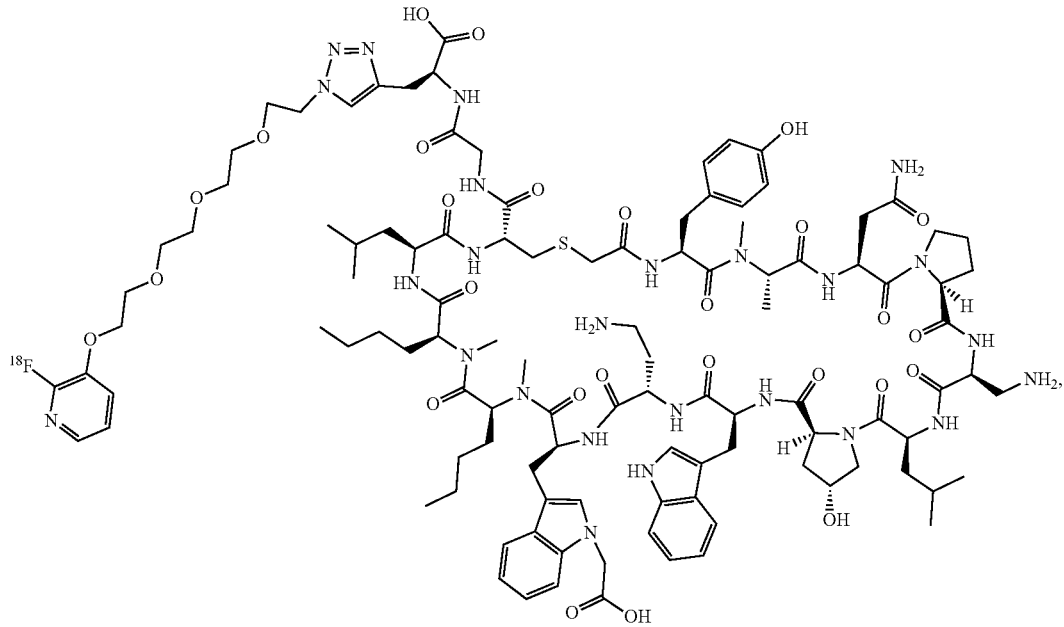

(III)

or a pharmaceutically acceptable salt thereof.

4. A pharmaceutical composition comprising a compound of claim 1 and a pharmaceutically acceptable carrier.

5. A method of obtaining an image of a compound of claim 1, the method comprising,
   a) administering the compound to a subject; and
   b) imaging in vivo the distribution of the compound positron emission tomography (PET) scanning.

6. The method of claim 5, wherein the imaged distribution of the compound is indicative of the presence or absence of a disease.

7. A method of monitoring the progress of a disease in a subject, the method comprising
   (a) administering to a subject in need thereof a compound of claim 1 which binds to a target molecule associated with the presence of the disease at a first time point and obtaining an image of at least a portion of the subject to determine an amount of diseased cells or tissue; and
   (b) administering to the subject a compound of claim 1 at one or more subsequent time points and obtaining an image of at least a portion of the subject at each time point; wherein the dimension and location of diseased cells or tissue at each time point is indicative of the progress of the disease.

8. The method of claim 7 wherein the disease is selected from the group consisting of solid cancers, hematopoietic cancers, hematological cancers, autoimmune disease, neurodegenerative disease cardiovascular disease, and pathogenic infection.

9. A method of quantifying diseased cells or tissues in a subject, the method comprising
   (a) administering to a subject having diseased cells or tissues a compound of claim 1 which binds to a target molecule located with the diseased cells or tissues; and
   (b) detecting radioactive emissions of the compound of claim 1 in the diseased cells or tissue, wherein the level and distribution of the radioactive emissions in the diseased cells or tissues is a quantitative measure of the diseased cells or tissues.

10. A method of obtaining a quantitative image of tissues or cells expressing PD-L1, the method comprising contacting the tissues or cells with a compound of claim 1 which binds to PD-L1, and detecting or quantifying the tissues or cells expressing PD-L1 using positron emission tomography (PET).

11. A method of screening for an agent that binds to PD-L1 comprising the steps of
    (a) contacting cells expressing PD-L1 with a compound of claim 1 which binds to PD-L1 in the presence and absence of a candidate agent; and
    (b) imaging the cells in the presence and absence of the candidate agent using positron emission tomography (PET),
wherein a decrease in the amount of radioactive emissions in the presence of the candidate agent is indicative that the candidate agent binds to PD-L1.

* * * * *